(12) United States Patent
Chen et al.

(10) Patent No.: US 12,405,252 B2
(45) Date of Patent: Sep. 2, 2025

(54) METHOD FOR DETECTING CONTENTS OF WHEY PROTEIN AND CASEIN, AND/OR RATIO THEREOF IN MILK POWDER

(71) Applicant: Beijing Sanyuan Foods Co., Ltd., Beijing (CN)

(72) Inventors: Lijun Chen, Beijing (CN); Tao Xu, Beijing (CN); Jingyao Chen, Beijing (CN); Weicang Qiao, Beijing (CN); Junying Zhao, Beijing (CN)

(73) Assignee: BEIJING SANYUAN FOODS CO., LTD., Beijing (CN)

( * ) Notice: Subject to any disclaimer, the term of this patent is extended or adjusted under 35 U.S.C. 154(b) by 656 days.

(21) Appl. No.: 17/871,549

(22) Filed: Jul. 22, 2022

(65) Prior Publication Data

US 2023/0080697 A1 Mar. 16, 2023

Related U.S. Application Data

(63) Continuation of application No. PCT/CN2021/143234, filed on Dec. 30, 2021.

(30) Foreign Application Priority Data

Aug. 6, 2021 (CN) .......................... 202110904028.8

(51) Int. Cl.
*G01N 30/06* (2006.01)
*G01N 30/30* (2006.01)
(Continued)

(52) U.S. Cl.
CPC ............. *G01N 30/06* (2013.01); *G01N 30/30* (2013.01); *G01N 30/34* (2013.01); *G01N 30/72* (2013.01); *G01N 30/88* (2013.01); *G01N 33/04* (2013.01)

(58) Field of Classification Search
CPC ........ G01N 30/06; G01N 30/30; G01N 30/34; G01N 30/72; G01N 30/88; G01N 33/04;
(Continued)

(56) References Cited

U.S. PATENT DOCUMENTS

2021/0088515 A1 3/2021 Paullin

FOREIGN PATENT DOCUMENTS

| CN | 108152385 A | * | 6/2018 | |
| CN | 108613965 A | * | 10/2018 | ............. G01N 21/65 |
| CN | 113341037 A | | 9/2021 | |

OTHER PUBLICATIONS

EPO Machine Translation of CN108152385A (Year: 2025).*
EPO Machine Translation or CN 108613965A (Year: 2025).*

\* cited by examiner

*Primary Examiner* — Jennifer Wecker
*Assistant Examiner* — Steven Ray Castaneda
(74) *Attorney, Agent, or Firm* — HAUPTMAN HAM, LLP

(57) ABSTRACT

The present disclosure relates to a method for detecting the contents of whey protein and casein, and/or the ratio thereof in milk powder by liquid chromatography-mass spectrometry. According to the method of the present disclosure, the characteristic peptide segments of whey protein and casein are selected and used for correction, and thus the accuracy and stability of detection of peptide segments by mass spectrometry using external standards are improved; in addition, the method of the present disclosure has the following advantages: easy to pretreat samples, low cost, a wide range of applicability, enable to perform quantitative detection of whey protein at one time, not affected by protein denaturation in the production process, no need to synthesize isotope internal standard, and avoiding influence of
(Continued)

ionization efficiency and matrix in mass spectrometry detection by means of their own multiple characteristic peptide segment ratios.

10 Claims, 9 Drawing Sheets

Specification includes a Sequence Listing.

(51) Int. Cl.
*G01N 30/34* (2006.01)
*G01N 30/72* (2006.01)
*G01N 30/88* (2006.01)
*G01N 33/04* (2006.01)

(58) Field of Classification Search
CPC .......... G01N 2030/8831; G01N 30/02; G01N 30/32; G01N 30/8675; G01N 2030/324
See application file for complete search history.

SEQUENCE LISTING

```
Sequence total quantity: 75
SEQ ID NO: 1                    moltype = AA   length = 8
FEATURE                         Location/Qualifiers
source                          1..8
                                mol_type = protein
                                organism = Bos taurus
SEQUENCE: 1
LDQWLCEK                                                                    8

SEQ ID NO: 2                    moltype = AA   length = 7
FEATURE                         Location/Qualifiers
source                          1..7
                                mol_type = protein
                                organism = Bos taurus
SEQUENCE: 2
VLPVPQK                                                                     7

SEQ ID NO: 3                    moltype = AA   length = 11
FEATURE                         Location/Qualifiers
source                          1..11
                                mol_type = protein
                                organism = Bos taurus
SEQUENCE: 3
TPEVDDEALE K                                                               11

SEQ ID NO: 4                    moltype = AA   length = 8
FEATURE                         Location/Qualifiers
source                          1..8
                                mol_type = protein
                                organism = Bos taurus
SEQUENCE: 4
FALPQYLK                                                                    8

SEQ ID NO: 5                    moltype = AA   length = 162
FEATURE                         Location/Qualifiers
source                          1..162
                                mol_type = protein
                                organism = Bos taurus
SEQUENCE: 5
LIVTQTMKGL DIQKVAGTWY SLAMAASDIS LLDAQSAPLR VYVEELKPTP EGDLEILLQK           60
WENDECAQKK IIAEKTKIPA VFKIDALNEN KVLVLDTDYK KYLLFCMENS AEPEQSLVCQ          120
CLVRTPEVDD EALEKFDKAL KALPMHIRLS FNPTQLEEQC HI                            162

SEQ ID NO: 6                    moltype = AA   length = 26
FEATURE                         Location/Qualifiers
source                          1..26
                                mol_type = protein
                                organism = Bos taurus
SEQUENCE: 6
VAGTWYSLAM AASDISLLDA QSAPLR                                               26

SEQ ID NO: 7                    moltype = AA   length = 23
FEATURE                         Location/Qualifiers
source                          1..23
                                mol_type = protein
                                organism = Bos taurus
SEQUENCE: 7
YLLFCMENSA EPEQSLVCQC LVR                                                  23

SEQ ID NO: 8                    moltype = AA   length = 20
FEATURE                         Location/Qualifiers
source                          1..20
                                mol_type = protein
                                organism = Bos taurus
SEQUENCE: 8
VYVEELKPTP EGDLEILLQK                                                      20

SEQ ID NO: 9                    moltype = AA   length = 14
FEATURE                         Location/Qualifiers
source                          1..14
                                mol_type = protein
                                organism = Bos taurus
SEQUENCE: 9
LSFNPTQLEE QCHI                                                            14

SEQ ID NO: 10                   moltype = AA   length = 11
FEATURE                         Location/Qualifiers
source                          1..11
```

```
                              mol_type = protein
                              organism = Bos taurus
SEQUENCE: 10
TPEVDDEALE K                                                        11

SEQ ID NO: 11                 moltype = AA   length = 9
FEATURE                       Location/Qualifiers
source                        1..9
                              mol_type = protein
                              organism = Bos taurus
SEQUENCE: 11
WENDECAQK                                                            9

SEQ ID NO: 12                 moltype = AA   length = 9
FEATURE                       Location/Qualifiers
source                        1..9
                              mol_type = protein
                              organism = Bos taurus
SEQUENCE: 12
VLVLDTDYK                                                            9

SEQ ID NO: 13                 moltype = AA   length = 8
FEATURE                       Location/Qualifiers
source                        1..8
                              mol_type = protein
                              organism = Bos taurus
SEQUENCE: 13
LIVTQTMK                                                             8

SEQ ID NO: 14                 moltype = AA   length = 8
FEATURE                       Location/Qualifiers
source                        1..8
                              mol_type = protein
                              organism = Bos taurus
SEQUENCE: 14
IDALNENK                                                             8

SEQ ID NO: 15                 moltype = AA   length = 7
FEATURE                       Location/Qualifiers
source                        1..7
                              mol_type = protein
                              organism = Bos taurus
SEQUENCE: 15
ALPMHIR                                                              7

SEQ ID NO: 16                 moltype = AA   length = 6
FEATURE                       Location/Qualifiers
source                        1..6
                              mol_type = protein
                              organism = Bos taurus
SEQUENCE: 16
IPAVFK                                                               6

SEQ ID NO: 17                 moltype = AA   length = 6
FEATURE                       Location/Qualifiers
source                        1..6
                              mol_type = protein
                              organism = Bos taurus
SEQUENCE: 17
GLDIQK                                                               6

SEQ ID NO: 18                 moltype = AA   length = 5
FEATURE                       Location/Qualifiers
source                        1..5
                              mol_type = protein
                              organism = Bos taurus
SEQUENCE: 18
IIAEK                                                                5

SEQ ID NO: 19                 moltype = AA   length = 123
FEATURE                       Location/Qualifiers
source                        1..123
                              mol_type = protein
                              organism = Bos taurus
SEQUENCE: 19
EQLTKCEVFR ELKDLKGYGG VSLPEWVCTT FHTSGYDTQA IVQNNDSTEY GLFQINNKIW    60
CKDDQNPHSS NICNISCDKF LDDDLTDDIM CVKKILDKVG INYWLAHKAL CSEKLDQWLC   120
EKL                                                                123
```

```
SEQ ID NO: 20              moltype = AA   length = 42
FEATURE                    Location/Qualifiers
source                     1..42
                           mol_type = protein
                           organism = Bos taurus
SEQUENCE: 20
GYGGVSLPEW VCTTFHTSGY DTQAIVQNND STEYGLFQIN NK                    42

SEQ ID NO: 21              moltype = AA   length = 17
FEATURE                    Location/Qualifiers
source                     1..17
                           mol_type = protein
                           organism = Bos taurus
SEQUENCE: 21
DDQNPHSSNI CNISCDK                                                17

SEQ ID NO: 22              moltype = AA   length = 14
FEATURE                    Location/Qualifiers
source                     1..14
                           mol_type = protein
                           organism = Bos taurus
SEQUENCE: 22
FLDDDLTDDI MCVK                                                   14

SEQ ID NO: 23              moltype = AA   length = 10
FEATURE                    Location/Qualifiers
source                     1..10
                           mol_type = protein
                           organism = Bos taurus
SEQUENCE: 23
VGINYWLAHK                                                        10

SEQ ID NO: 24              moltype = AA   length = 8
FEATURE                    Location/Qualifiers
source                     1..8
                           mol_type = protein
                           organism = Bos taurus
SEQUENCE: 24
LDQWLCEK                                                          8

SEQ ID NO: 25              moltype = AA   length = 5
FEATURE                    Location/Qualifiers
source                     1..5
                           mol_type = protein
                           organism = Bos taurus
SEQUENCE: 25
CEVFR                                                             5

SEQ ID NO: 26              moltype = AA   length = 6
FEATURE                    Location/Qualifiers
source                     1..6
                           mol_type = protein
                           organism = Bos taurus
SEQUENCE: 26
ALCSEK                                                            6

SEQ ID NO: 27              moltype = AA   length = 5
FEATURE                    Location/Qualifiers
source                     1..5
                           mol_type = protein
                           organism = Bos taurus
SEQUENCE: 27
EQLTK                                                             5

SEQ ID NO: 28              moltype = AA   length = 4
FEATURE                    Location/Qualifiers
source                     1..4
                           mol_type = protein
                           organism = Bos taurus
SEQUENCE: 28
IWCK                                                              4

SEQ ID NO: 29              moltype = AA   length = 163
FEATURE                    Location/Qualifiers
source                     1..163
                           mol_type = protein
                           organism = Bos taurus
SEQUENCE: 29
MKLLILTCLV AVALARPKHP IKHQGLPQEV LNENLLRFFV APFPEVFGKE KVNELSKDIG  60
```

```
SESTEDQAME DIKQMEAESI SSSEEIVPNS VEQKHIQKED VPSERYLGYL EQLLRLKKYK    120
VPQLEIVPNS AEERLHSMKE GIHAQQKEPM IGVNQELAYF YPE                     163

SEQ ID NO: 30           moltype = AA  length = 21
FEATURE                 Location/Qualifiers
source                  1..21
                        mol_type = protein
                        organism = Bos taurus
SEQUENCE: 30
QMEAESISSS EEIVPNSVEQ K                                              21

SEQ ID NO: 31           moltype = AA  length = 16
FEATURE                 Location/Qualifiers
source                  1..16
                        mol_type = protein
                        organism = Bos taurus
SEQUENCE: 31
EPMIGVNQEL AYFYPE                                                    16

SEQ ID NO: 32           moltype = AA  length = 16
FEATURE                 Location/Qualifiers
source                  1..16
                        mol_type = protein
                        organism = Bos taurus
SEQUENCE: 32
DIGSESTEDQ AMEDIK                                                    16

SEQ ID NO: 33           moltype = AA  length = 15
FEATURE                 Location/Qualifiers
source                  1..15
                        mol_type = protein
                        organism = Bos taurus
SEQUENCE: 33
HQGLPQEVLN ENLLR                                                     15

SEQ ID NO: 34           moltype = AA  length = 16
FEATURE                 Location/Qualifiers
source                  1..16
                        mol_type = protein
                        organism = Bos taurus
SEQUENCE: 34
LLILTCLVAV ALARPK                                                    16

SEQ ID NO: 35           moltype = AA  length = 14
FEATURE                 Location/Qualifiers
source                  1..14
                        mol_type = protein
                        organism = Bos taurus
SEQUENCE: 35
VPQLEIVPNS AEER                                                      14

SEQ ID NO: 36           moltype = AA  length = 12
FEATURE                 Location/Qualifiers
source                  1..12
                        mol_type = protein
                        organism = Bos taurus
SEQUENCE: 36
FFVAPFPEVF GK                                                        12

SEQ ID NO: 37           moltype = AA  length = 10
FEATURE                 Location/Qualifiers
source                  1..10
                        mol_type = protein
                        organism = Bos taurus
SEQUENCE: 37
YLGYLEQLLR                                                           10

SEQ ID NO: 38           moltype = AA  length = 8
FEATURE                 Location/Qualifiers
source                  1..8
                        mol_type = protein
                        organism = Bos taurus
SEQUENCE: 38
EGIHAQQK                                                              8

SEQ ID NO: 39           moltype = AA  length = 7
FEATURE                 Location/Qualifiers
source                  1..7
                        mol_type = protein
```

```
                                organism = Bos taurus
SEQUENCE: 39
EDVPSER                                                              7

SEQ ID NO: 40           moltype = AA   length = 6
FEATURE                 Location/Qualifiers
source                  1..6
                        mol_type = protein
                        organism = Bos taurus
SEQUENCE: 40
VNELSK                                                               6

SEQ ID NO: 41           moltype = AA   length = 5
FEATURE                 Location/Qualifiers
source                  1..5
                        mol_type = protein
                        organism = Bos taurus
SEQUENCE: 41
LHSMK                                                                5

SEQ ID NO: 42           moltype = AA   length = 4
FEATURE                 Location/Qualifiers
source                  1..4
                        mol_type = protein
                        organism = Bos taurus
SEQUENCE: 42
HIQK                                                                 4

SEQ ID NO: 43           moltype = AA   length = 222
FEATURE                 Location/Qualifiers
source                  1..222
                        mol_type = protein
                        organism = Bos taurus
SEQUENCE: 43
MKFFIFTCLL AVALAKNTME HVSSSEESII SQETYKGEKN MAINPSKENL CSTFCKEVVR      60
NANEEEYSIG SSSEESAEVA TEEVKITVDD KHYQKALNEI NQFYQKFPQY LQYLYQGPIV     120
LNPWDQVKRN AVPITPTLNR EQLSTSEENS KKTVDMESTE VFTKKTKLTE EEKNRLNFLK     180
KISQRYQKFA LPQYLKTVYQ HQKAMKPWIQ PKTKVIPYVR YL                       222

SEQ ID NO: 44           moltype = AA   length = 22
FEATURE                 Location/Qualifiers
source                  1..22
                        mol_type = protein
                        organism = Bos taurus
SEQUENCE: 44
FPQYLQYLYQ GPIVLNPWDQ VK                                             22

SEQ ID NO: 45           moltype = AA   length = 25
FEATURE                 Location/Qualifiers
source                  1..25
                        mol_type = protein
                        organism = Bos taurus
SEQUENCE: 45
NANEEEYSIG SSSEESAEVA TEEVK                                          25

SEQ ID NO: 46           moltype = AA   length = 20
FEATURE                 Location/Qualifiers
source                  1..20
                        mol_type = protein
                        organism = Bos taurus
SEQUENCE: 46
NTMEHVSSSE ESIISQETYK                                                20

SEQ ID NO: 47           moltype = AA   length = 14
FEATURE                 Location/Qualifiers
source                  1..14
                        mol_type = protein
                        organism = Bos taurus
SEQUENCE: 47
FFIFTCLLAV ALAK                                                      14

SEQ ID NO: 48           moltype = AA   length = 12
FEATURE                 Location/Qualifiers
source                  1..12
                        mol_type = protein
                        organism = Bos taurus
SEQUENCE: 48
TVDMESTEVF TK                                                        12
```

| | | |
|---|---|---|
| SEQ ID NO: 49<br>FEATURE<br>source | moltype = AA   length = 11<br>Location/Qualifiers<br>1..11<br>mol_type = protein<br>organism = Bos taurus | |
| SEQUENCE: 49<br>ALNEINQFYQ K | | 11 |
| SEQ ID NO: 50<br>FEATURE<br>source | moltype = AA   length = 11<br>Location/Qualifiers<br>1..11<br>mol_type = protein<br>organism = Bos taurus | |
| SEQUENCE: 50<br>EQLSTSEENS K | | 11 |
| SEQ ID NO: 51<br>FEATURE<br>source | moltype = AA   length = 11<br>Location/Qualifiers<br>1..11<br>mol_type = protein<br>organism = Bos taurus | |
| SEQUENCE: 51<br>NAVPITPTLN R | | 11 |
| SEQ ID NO: 52<br>FEATURE<br>source | moltype = AA   length = 9<br>Location/Qualifiers<br>1..9<br>mol_type = protein<br>organism = Bos taurus | |
| SEQUENCE: 52<br>AMKPWIQPK | | 9 |
| SEQ ID NO: 53<br>FEATURE<br>source | moltype = AA   length = 9<br>Location/Qualifiers<br>1..9<br>mol_type = protein<br>organism = Bos taurus | |
| SEQUENCE: 53<br>ENLCSTFCK | | 9 |
| SEQ ID NO: 54<br>FEATURE<br>source | moltype = AA   length = 8<br>Location/Qualifiers<br>1..8<br>mol_type = protein<br>organism = Bos taurus | |
| SEQUENCE: 54<br>FALPQYLK | | 8 |
| SEQ ID NO: 55<br>FEATURE<br>source | moltype = AA   length = 7<br>Location/Qualifiers<br>1..7<br>mol_type = protein<br>organism = Bos taurus | |
| SEQUENCE: 55<br>TVYQHQK | | 7 |
| SEQ ID NO: 56<br>FEATURE<br>source | moltype = AA   length = 8<br>Location/Qualifiers<br>1..8<br>mol_type = protein<br>organism = Bos taurus | |
| SEQUENCE: 56<br>NMAINPSK | | 8 |
| SEQ ID NO: 57<br>FEATURE<br>source | moltype = AA   length = 6<br>Location/Qualifiers<br>1..6<br>mol_type = protein<br>organism = Bos taurus | |
| SEQUENCE: 57<br>LTEEEK | | 6 |
| SEQ ID NO: 58<br>FEATURE<br>source | moltype = AA   length = 6<br>Location/Qualifiers<br>1..6<br>mol_type = protein<br>organism = Bos taurus | |
| SEQUENCE: 58<br>VIPYVR | | 6 |

```
SEQ ID NO: 59            moltype = AA   length = 6
FEATURE                  Location/Qualifiers
source                   1..6
                         mol_type = protein
                         organism = Bos taurus
SEQUENCE: 59
ITVDDK                                                                    6

SEQ ID NO: 60            moltype = AA   length = 5
FEATURE                  Location/Qualifiers
source                   1..5
                         mol_type = protein
                         organism = Bos taurus
SEQUENCE: 60
LNFLK                                                                     5

SEQ ID NO: 61            moltype = AA   length = 4
FEATURE                  Location/Qualifiers
source                   1..4
                         mol_type = protein
                         organism = Bos taurus
SEQUENCE: 61
HYQK                                                                      4

SEQ ID NO: 62            moltype = AA   length = 4
FEATURE                  Location/Qualifiers
source                   1..4
                         mol_type = protein
                         organism = Bos taurus
SEQUENCE: 62
ISQR                                                                      4

SEQ ID NO: 63            moltype = AA   length = 4
FEATURE                  Location/Qualifiers
source                   1..4
                         mol_type = protein
                         organism = Bos taurus
SEQUENCE: 63
EVVR                                                                      4

SEQ ID NO: 64            moltype = AA   length = 224
FEATURE                  Location/Qualifiers
source                   1..224
                         mol_type = protein
                         organism = Bos taurus
SEQUENCE: 64
MKVLILACLV ALALARELEE LNVPGEIVES LSSSEESITR INKKIEKFQS EEQQQTEDEL   60
QDKIHPFAQT QSLVYPFPGP IHNSLPQNIP PLTQTPVVVP PFLQPEVMGV SKVKEAMAPK  120
HKEMPFPKYP VEPFTESQSL TLTDVENLHL PLPLLQSWMH QPHQPLPPTV MFPPQSVLSL  180
SQSKVLPVPQ KAVPYPQRDM PIQAFLLYQE PVLGPVRGPF PIIV                  224

SEQ ID NO: 65            moltype = AA   length = 56
FEATURE                  Location/Qualifiers
source                   1..56
                         mol_type = protein
                         organism = Bos taurus
SEQUENCE: 65
YPVEPFTESQ SLTLTDVENL HLPLPLLQSW MHQPHQPLPP TVMFPPQSVL SLSQSK       56

SEQ ID NO: 66            moltype = AA   length = 49
FEATURE                  Location/Qualifiers
source                   1..49
                         mol_type = protein
                         organism = Bos taurus
SEQUENCE: 66
IHPFAQTQSL VYPFPGPIHN SLPQNIPPLT QTPVVVPPFL QPEVMGVSK              49

SEQ ID NO: 67            moltype = AA   length = 24
FEATURE                  Location/Qualifiers
source                   1..24
                         mol_type = protein
                         organism = Bos taurus
SEQUENCE: 67
ELEELNVPGE IVESLSSSEE SITR                                         24

SEQ ID NO: 68            moltype = AA   length = 19
FEATURE                  Location/Qualifiers
source                   1..19
```

| | | |
|---|---|---|
| | mol_type = protein<br>organism = Bos taurus | |
| SEQUENCE: 68<br>DMPIQAFLLY QEPVLGPVR | | 19 |
| SEQ ID NO: 69<br>FEATURE<br>source | moltype = AA  length = 16<br>Location/Qualifiers<br>1..16<br>mol_type = protein<br>organism = Bos taurus | |
| SEQUENCE: 69<br>FQSEEQQQTE DELQDK | | 16 |
| SEQ ID NO: 70<br>FEATURE<br>source | moltype = AA  length = 14<br>Location/Qualifiers<br>1..14<br>mol_type = protein<br>organism = Bos taurus | |
| SEQUENCE: 70<br>VLILACLVAL ALAR | | 14 |
| SEQ ID NO: 71<br>FEATURE<br>source | moltype = AA  length = 7<br>Location/Qualifiers<br>1..7<br>mol_type = protein<br>organism = Bos taurus | |
| SEQUENCE: 71<br>AVPYPQR | | 7 |
| SEQ ID NO: 72<br>FEATURE<br>source | moltype = AA  length = 7<br>Location/Qualifiers<br>1..7<br>mol_type = protein<br>organism = Bos taurus | |
| SEQUENCE: 72<br>VLPVPQK | | 7 |
| SEQ ID NO: 73<br>FEATURE<br>source | moltype = AA  length = 6<br>Location/Qualifiers<br>1..6<br>mol_type = protein<br>organism = Bos taurus | |
| SEQUENCE: 73<br>EMPFPK | | 6 |
| SEQ ID NO: 74<br>FEATURE<br>source | moltype = AA  length = 7<br>Location/Qualifiers<br>1..7<br>mol_type = protein<br>organism = Bos taurus | |
| SEQUENCE: 74<br>GPFPIIV | | 7 |
| SEQ ID NO: 75<br>FEATURE<br>source | moltype = AA  length = 6<br>Location/Qualifiers<br>1..6<br>mol_type = protein<br>organism = Bos taurus | |
| SEQUENCE: 75<br>EAMAPK | | 6 |

METHOD FOR DETECTING CONTENTS OF WHEY PROTEIN AND CASEIN, AND/OR RATIO THEREOF IN MILK POWDER

RELATED APPLICATIONS

The present application is a U.S. Continuation Application of International Application NO. PCT/CN2021/143234 filed Dec. 30, 2021, and claims priority to Chinese Application Number 202110904028.8, filed Aug. 6, 2021, the disclosures of which are hereby incorporated by reference herein in their entireties.

INCORPORATION BY REFERENCE sequence listing provided in the file entitled C6160-022_SQL_v2.xml, which is an Extensible Markup Language (XML) file that was created on Nov. 13, 2022, and which comprises 66,298 bytes, is hereby incorporated by reference in its entirety.

TECHNICAL FIELD

The present disclosure relates to the technical field of food detection, and in particular to a method for detecting the contents of whey protein and casein, and/or the ratio thereof in milk powder by liquid chromatography-mass spectrometry.

BACKGROUND ART

Whey protein, as one of the main nutrients in infant formula milk powder, accounts for a particularly important nutritional proportion of the formula milk powder. The main ingredients of whey protein are shown in the following table:

TABLE 1

Main ingredients of whey protein

| Whey protein | Proportion (%) | Relative molecular mass | Isoelectric point | Function |
|---|---|---|---|---|
| α-La | 20~25% | 14.2 | 4.20-4.50 | binding to metal ions including calcium; contributing to the transportation and absorption of calcium; participating in the synthesis of lactose; regulating neurotransmitters to help sleep; promoting infant brain development; having anti-cancer effect. |
| β-Lg | 50-55% | 18.3 | 5.35-5.49 | binding to fat-soluble vitamins and fatty acids and transporting them; participating in the synthesis of prostaglandin-related enzymes, and having antihypertensive and antitumor effects. |
| Ig | 10-15% | <150.0 | 5.50-8.30 | resisting to microbial pathogens and toxins, and being one important component of human immunity; being able to protect breast from infection. |
| BSA | 5-10% | 66.4 | 5.13 | participating in the transport, metabolism, and distribution of ligands; regulating blood osmotic pressure. |

Whey protein contains a variety of essential amino acids required by human body and exhibits high bioavailability. It contains one third of branched-chain amino acids (leucine, isoleucine, and valine, etc.), which not only provide energy for the body, but also have been proved to be one of the important precursors for the synthesis of glutamate in human body. In addition, leucine can also participate in the intracellular metabolic pathways regulating synthesis of skeletal muscle protein, thus enhancing the synthesis of skeletal muscle protein.

Whey protein is also an important source of sulfur-containing amino acids (cysteine) in human body, which are important precursors for making up glutathione and taurine. Glutathione plays a key role in free radical scavenging and immune response. Glutathione, as well as taurine, can inhibit lipid peroxidation and play an antioxidant role. Threonine in whey protein is converted directly into intestinal mucin after being taken up by intestinal tract, thus providing protection for intestinal cells as well as intestinal barrier integrity. Finally, lysine and arginine in whey protein can promote muscle growth by stimulating secretion of metabolic hormones in the body.

As an important detection index for formula milk powder, it is stipulated by the national food safety standard GB 10765-2010 that the content of whey protein in infant formula milk powder should exceed 60%. Due to the complex additives in infant formula milk powder and the heating process in the production thereof, changes in the space structures of whey and casein proteins may occur, for example, a disulfide bond unfolds, resulting in protein aggregation, and thus forming polymers of various proteins, which makes the detection of whey protein in formula milk powder extremely difficult.

At present, many methods have been applied to detect the content of whey protein. However, among these methods, sodium dodecyl sulfate-polyacrylamide gel electrophoresis, high performance liquid chromatography, high performance capillary electrophoresis, etc., are all affected by protein denaturation occurred in the production thereof, resulting in an inaccurate quantification of whey protein, i.e., a large deviation in the measurement results; the amino acid conversion method, which is usually used to determine the content of whey protein, has a narrow application range and is easily affected by additives; and the liquid chromatography detection method using isotope internal standard cannot be widely used in practical production due to the need to synthesize internal standard isotopes which produces high detection cost.

Casein protein is one of the main proteins in milk and can be hydrolyzed into a variety of bioactive peptides after being digested in gastrointestinal tract. At present, detection of casein protein in formula milk powder is mainly performed by high performance liquid chromatography, in which, however, casein protein shows a less desirable peak shape in high performance liquid phase, and it is difficult to distinguish the chromatographic peak of κ-casein from that of a S2-casein. Enzyme-linked immunosorbent assay (ELISA) and liquid chromatography-mass spectrometry (LC-MS) and the like have also been proposed in succession, and they show a good performance in the detection of casein protein.

The information disclosed in the Background section is only intended to facilitate understanding of the general background of the present disclosure and should not be taken as an acknowledgment or implying, in any form, that the information constitutes the prior art already known to a person with ordinary skill in the art.

SUMMARY OF THE INVENTION

Purpose

In view of the disadvantages of the current detection methods as mentioned above, the present disclosure aims to provide a method for detecting the contents of whey protein and casein, and/or the ratio thereof in milk powder by liquid chromatography-mass spectrometry. According to the method of the present disclosure, the accuracy and stability of detecting peptide segments by mass spectrometry using external standard scan be improved by selecting the respective characteristic peptide segments of whey protein and casein and using the same for correction.

Solutions

In order to achieve the purpose of the invention, the technical solutions provided by the present disclosure are as follows.

In one aspect, provided is a method for detecting the contents of whey protein and casein, and/or the ratio thereof in milk powder by liquid chromatography-mass spectrometry, which comprises:

1) preparing a standard solution of whey protein with the characteristic peptide segments of α-lactalbumin and β-lactoglobulin, in accordance with the α-lactalbumin and β-lactoglobulin accounting for 20% and 50% of the whey protein, respectively;
2) preparing a standard solution of casein protein with the characteristic peptide segments of α-casein and β-casein, in accordance with the α-casein and β-casein accounting for 50% and 40% of the casein protein, respectively;
3) mixing the standard solution of whey protein from step 1) with the standard solution of casein protein from step 2) to prepare a series of mixed protein standard solutions with a series of whey protein:casein ratios;
4) drawing standard curves with the ratios of whey protein to casein as abscissa and the peak area ratios of characteristic peptide segments of α-lactalbumin to β-casein and those of β-lactoglobulin to α-casein as ordinate;
5) detecting the milk powder to be tested for the peak area ratios of characteristic peptide segments of β-lactoglobulin to α-casein and those of α-lactalbumin to β-casein;
6) substituting the peak area ratio of the characteristic peptide segments of β-lactoglobulin to α-casein in the detected milk powder into the standard curve to determine the ratio M of whey protein to casein, and calculate the actual amounts of β-lactoglobulin and α-casein based on the ratio M thus determined;
and, substituting the peak area ratio of the characteristic peptide segments of α-lactalbumin to β-casein in the detected milk powder into the standard curve to determine the ratio N of whey protein to casein, and calculate the actual amounts of α-lactalbumin to β-casein based on the ratio N thus determined;
7) acquiring the actual contents of whey protein and casein, and/or the actual ratio of whey protein/casein based on the actual amounts of α-lactalbumin, β-casein, β-lactoglobulin, and α-casein obtained from step 6).

In the above method, preferably, the characteristic peptide segments of α-lactalbumin, β-casein, β-lactoglobulin, and α-casein are LDQWLCEK shown in SEQ ID NO. 1, VLPVPQK shown in SEQ ID NO. 2, TPEVDDEALEK shown in SEQ ID NO. 3, and FALPQYLK shown in SEQ ID NO. 4, respectively.

Preferably, in step 3), the series of whey protein:casein ratios include whey protein:casein ratios of 0.25, 0.43, 0.67, 1, 1.5, and 2.33, respectively.

Preferably, in step 6), the actual amounts of β-lactoglobulin and α-casein are calculated by the following formulas, respectively:

$$\beta\text{-lactoglobulin} = \frac{M1}{M1 + M2} X * 50\%, \alpha\text{-casein} = \frac{M2}{M1 + M2} X * 50\%;$$

wherein, M1 is the preceding term in the ratio M of whey protein:casein as determined based on the peak area ratio of characteristic peptide segments of β-lactoglobulin to α-casein, and M2 is the latter term in the ratio M of whey protein:casein as determined based on the peak area ratio of characteristic peptide segments of β-lactoglobulin to α-casein, with the provisions of: M=M1/M2, and M1+M2=1; and, wherein, X is the total protein concentration of the sample.

Preferably, in step 6), the actual amounts of α-lactalbumin and β-casein are calculated by the following formulas:

$$\alpha\text{-}la = \frac{N1}{N1 + N2} X * 20\%, \beta\text{-}cs = \frac{N2}{N1 + N2} X * 40\%;$$

wherein, N1 is the preceding term in the ratio N of whey protein:casein as determined based on the peak area ratio of characteristic peptide segments of α-lactalbumin to β-casein, and N2 is the latter term in the ratio N of whey protein:casein as determined based on the peak area ratio of characteristic peptide segments of α-lactalbumin to β-casein, with the provisions of: N=N1/N2, and N1+N2=1; and, wherein, X is the total protein concentration of the sample.

Preferably, in step 7),
the formula for calculating the actual content of whey protein is:

$$\frac{\frac{N1}{N1+N2}X*20\% + \frac{M1}{M1+M2}X*50\%}{0.7}$$

the formula for calculating the actual content of casein is:

$$\frac{\frac{M2}{M1+M2}X*50\% + \frac{N2}{N1+N2}X*40\%}{0.9}$$

the formula for calculating the actual ratio of whey protein/casein is:

$$\frac{\frac{N1}{N1+N2}X*20\% + \frac{M1}{M1+M2}X*50\%}{0.7} / $$
$$\frac{\frac{M2}{M1+M2}X*50\% + \frac{N2}{N1+N2}X*40\%}{0.9} = $$
$$\frac{18N1+45M1}{35M2+28N2} = \frac{63MN+18N+45M}{35N+28M+63};$$

wherein, M1 is the preceding term in the ratio M of whey protein:casein as determined based on the peak area ratio of characteristic peptide segments of β-lactoglobulin to α-casein, and M2 is the latter term in the ratio M of whey protein:casein as determined based on the peak area ratio of characteristic peptide segments of β-lactoglobulin to α-casein, with the provisions of: M=M1/M2, and M1+M2=1;

wherein, N1 is the preceding term in the ratio N of whey protein:casein as determined based on the peak area ratio of characteristic peptide segments of α-lactalbumin to β-casein, and N2 is the latter term in the ratio N of whey protein:casein as determined based on the peak area ratio of characteristic peptide segments of α-lactalbumin to β-casein, with the provisions of: N=N1/N2, and N1+N2=1; and, wherein, X is the total protein concentration of the sample.

Preferably, the detection in step 5) comprises the steps of sample treatment and enzyme digestion:

dissolving the milk powder sample to be tested into a sample solution with a protein concentration of 0.1-0.4 mg/mL, preferably 0.2 mg/mL; subjecting the sample solution to rough filtration with a pure acetic acid filter membrane preferably with a pore size of 0.45 μm; adding the roughly filtered sample solution into ammonium bicarbonate solution, followed by adding dithiothreitol solution, and standing in a water bath at 65-75° C., preferably 70° C. for 25-35 min, preferably 30 min; after cooling, adding iodoacetamide solution, and standing for 25-35 min, preferably 30 min in the dark; illuminating the mixture for 8-12 min, preferably 10 min, followed by adding calcium chloride solution; then adding trypsin solution to allow an enzyme digestion at 37° C. for 26-30 h; then adding acetic acid solution to stop the enzyme digestion; filtering the reaction mixture with polyethersulfone filter membrane, and then performing selective ion scanning analysis by mass spectrometry.

In a specific embodiment, the upper detection limit of the method of the present disclosure is at a total protein concentration of 0.4 mg/mL.

In a second aspect, provided is a combination of characteristic peptide segments for detecting the ratio of whey protein:casein by liquid chromatography-mass spectrometry, comprising: characteristic peptide segments of α-lactalbumin, β-casein, β-lactoglobulin, and α-casein with amino acid sequences as shown in SEQ ID NO. 1, SEQ ID NO. 2, SEQ ID NO. 3, and SEQ ID NO. 4, respectively.

In a specific embodiment, the combination of characteristic peptide segments consists of characteristic peptide segments of α-lactalbumin, β-casein, β-lactoglobulin, and α-casein with amino acid sequences as shown in SEQ ID NO. 1, SEQ ID NO. 2, SEQ ID NO. 3 and SEQ ID NO. 4, respectively.

Beneficial Effects

Compared with the prior art, the relative quantitative method for detecting the contents of whey protein and casein, and/or the ratio thereof in milk powder has high accuracy and stability, and in addition, it has the following advantages: easy to pretreat samples, low cost, a wide range of applicability, enable to perform quantitative detection of whey protein at one time, not affected by protein denaturation in the production process, no need to synthesize isotope internal standard, and avoiding influence of ionization efficiency and matrix in mass spectrometry detection by means of their own multiple characteristic peptide segment ratios.

BRIEF DESCRIPTION OF THE DRAWINGS

One or more examples are exemplified by the pictures in the accompanying drawings that correspond thereto and are not intended to be limiting of the embodiments. As used herein, the word "exemplary" means "serving as an example, embodiment, or illustrative". Any embodiment described herein as "exemplary" is not necessarily to be construed as superior or better than other embodiments.

DETAILED DESCRIPTION OF THE INVENTION

Figure 1:
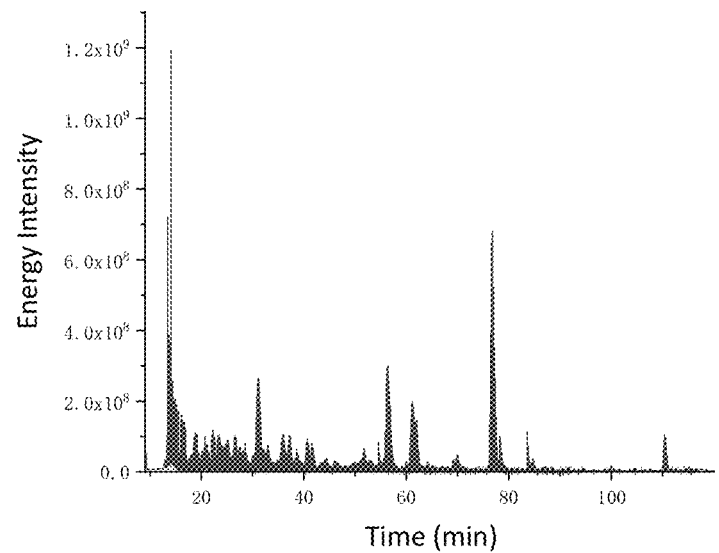
FIG. 1 is a full scanning mass spectrum of the mixed standard substance used in the Example.

In order to make the purpose, technical solutions, and advantages of the embodiments of the invention clearer, the technical solutions in the embodiments of the present disclosure will be described clearly and completely, obviously, the described embodiments are some of the embodiments of the present disclosure, but not all of them. Based on the embodiments of the present disclosure, all other embodiments obtained by those of ordinary skill in the art without creative work are within the scope of the present invention.

In addition, in order to better explain the present invention, a lot of specific details are given in the following embodiments. It will be understood by those skilled in the art that the present invention may be practiced without certain specific details. In some embodiments, materials, elements, methods, means, etc., well known to those skilled in the art, are not described in detail so as to highlight the spirit of the present invention.

Throughout the specification and claims, the term "comprising" or variations thereof, such as "including" or "containing" and the like, will be understood to include the stated components and not to exclude other elements or other components, unless expressly indicated otherwise.

In the following examples, the reagents used were as follows:

Dithiothreitol (sigma, ≥98% HPLC); iodoacetamide (sigma, ≥99% NMR); α-lactalbumin standard substance (sigma, ≥85%); β-lactoglobulin standard substance (sigma, ≥90%); α-casein standard substance (sigma, ≥70%); β-casein standard substance (sigma, ≥98%); bovine basic trypsin (sigma, ≥10,000 BAEE); Calcium chloride (AR); Ammonium bicarbonate (AR); Acetic acid (AR).

In the following examples, nano-high-performance liquid chromatography-orbitrap high resolution mass spectrometry (NanoLC-Orbitrap MS) was used for selective ion scanning analysis under the following chromatographic conditions:

Nano-high-performance liquid UltiMate 3000 (ACCELA)

Column: Acclaim® PepMap RSLC (75 μm×15 cm, nano Viper C18, 2 μm, 100 A Thermo Fisher Scientific); Acclaim PepMap™ 100 (75 μm×2 cm, nanoViper C18, 3 μm, 100 A Thermo Fisher Scientific)

Column temperature: 50° C.

Mobile phase A: 2% acetonitrile+98% water+0.1% formic acid

Mobile phase B: 80% acetonitrile+20% water+0.1% formic acid

Loading: 2% acetonitrile+98% water

Flow rate: NC: 0.25 μL/min, loading flow rate: 0.3 μL/min

Injection volume: 1 μL

Gradient elution conditions

Gradient elution

| Elution time (min) | Flow rate (μL/min) | A % | B % |
| --- | --- | --- | --- |
| 0 | 0.25 | 96 | 4 |
| 5 | 0.25 | 96 | 4 |
| 65 | 0.25 | 78 | 22 |
| 70 | 0.25 | 10 | 90 |
| 75 | 0.25 | 96 | 4 |
| 76 | 0.25 | 96 | 4 |

In the following examples, the characteristic peptide segments were subjected to a mass spectrometry analysis in PRM mode under the following mass spectrometry conditions:

Q Exactive mass spectrometer (Thermo Fisher Scientific)

PRM mode

Running time: 5-75 min

Polarity: positive

Resolution: 17500

AGC target: 1e5

Maximum IT: 100 ms

Separation window: 1.0 m/z

Initial mass-to-charge ratio: Fixed first mass

NCE: 27%, 28%.

Example 1: Selection of Characteristic Peptide Segments

Figure 2:
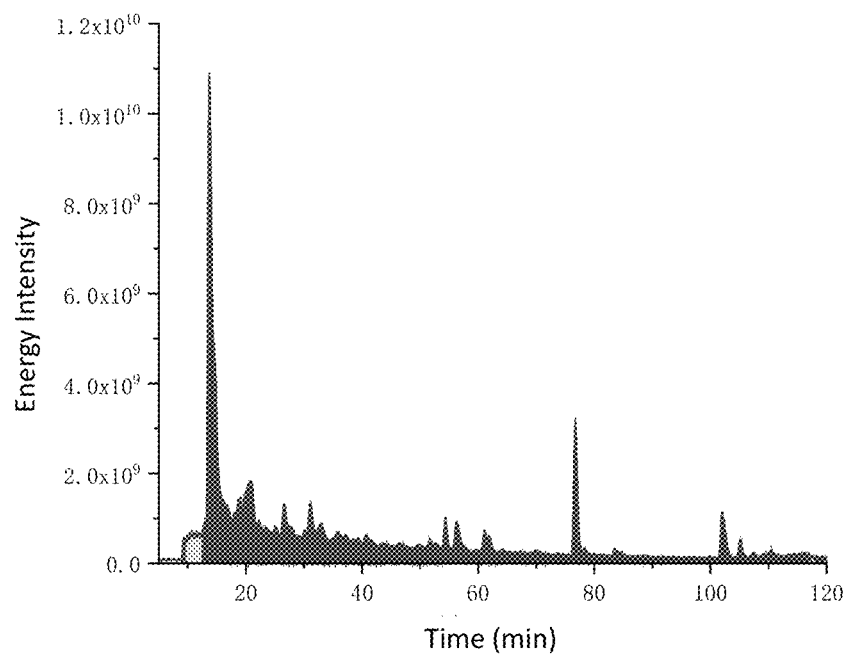
FIG. 2 is a full scanning mass spectrum of the milk powder sample.

A mixed standard substance of α-lactalbumin, β-lactoglobulin, α-casein, and β-casein and a milk powder sample were subjected to a full-scanning by mass spectrometry, and the mass spectra thereof were shown in FIG. 1 and FIG. 2, respectively.

By using ExPASyPeptideMass website, four proteins obtained by retrieval in NCBI's database, α-lactalbumin, β-lactoglobulin, α-casein, and β-casein, were subjected to a simulated enzyme digestion (for the peptide segments produced by the simulated digestion, please see Table 2 below), and a comparation. The compared peptide segments were substituted to NCBI website for BLAST alignment analysis, and peptide segments with high response value and a sequence length of 5-25 amino acids were selected and finally determined as the specific peptide segments, which were:

characteristic peptide segment of α-lactalbumin (hereinafter also referred to as α-la) LDQWLCEK (SEQ ID NO. 1), characteristic peptide segment of β-lactoglobulin (hereinafter also referred to as β-lg) TPEVDDEALEK (SEQ ID NO. 3), characteristic peptide segment of α-casein (hereinafter also referred to as α-cs) FALPQYLK (SEQ ID NO. 4), characteristic peptide segment of β-casein (hereinafter also referred to as β-cs) VLPVPQK (SEQ ID NO. 2).

Figure 3:
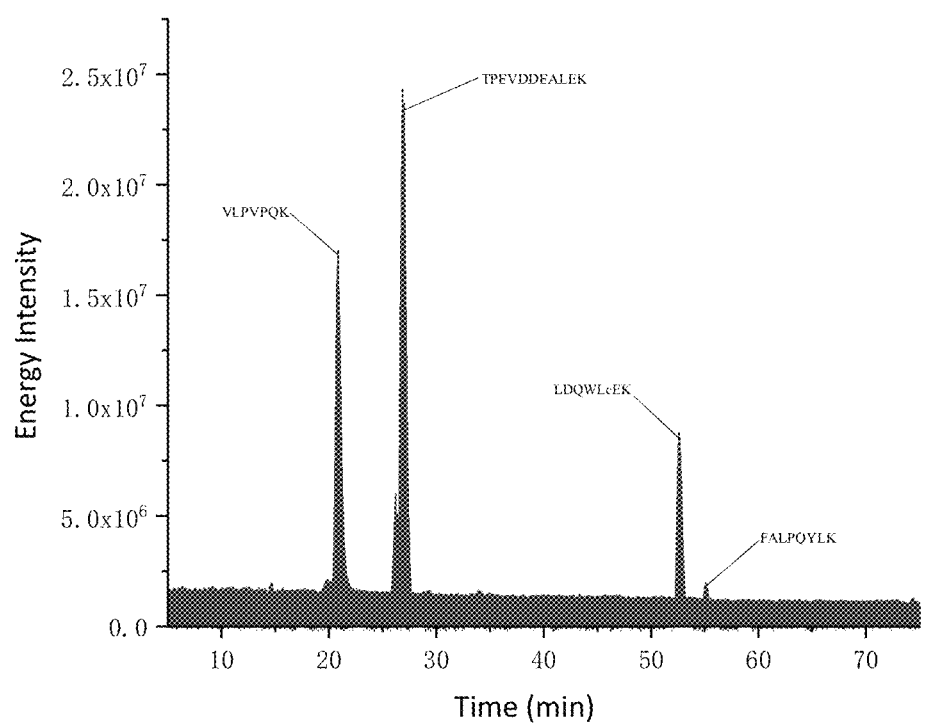
FIG. 3 is the mass spectrum of four characteristic peptide segments in PRM mode.
Figure 4:
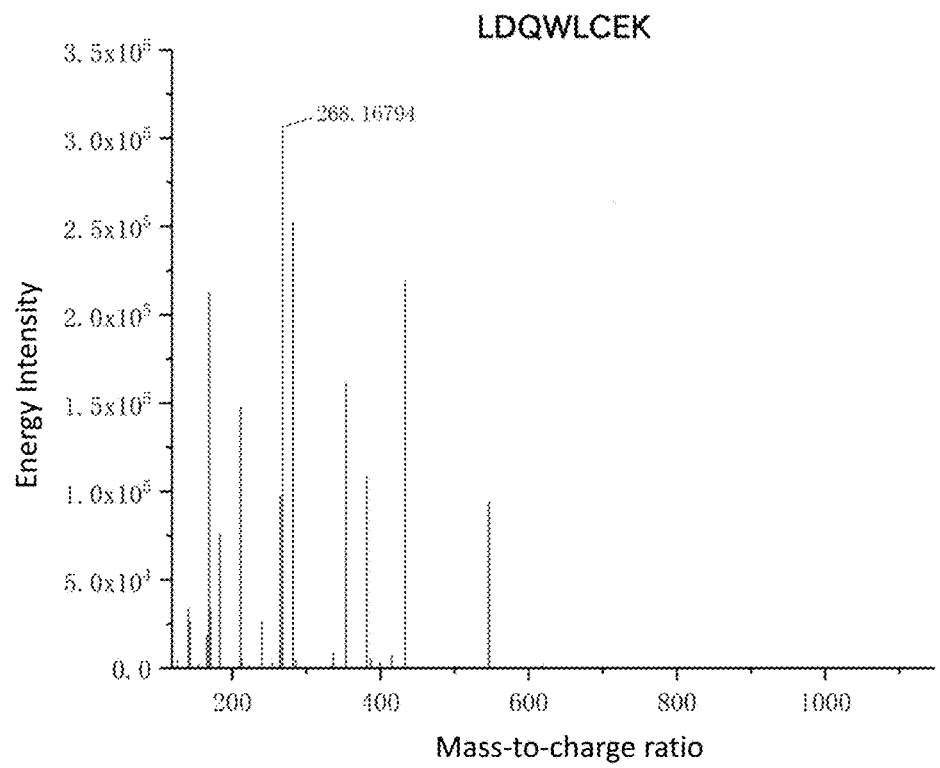
FIG. 4 is the full fragment ion diagram of the characteristic peptide segment (LDQWLCEK) shown in SEQ ID NO. 1.
Figure 5:
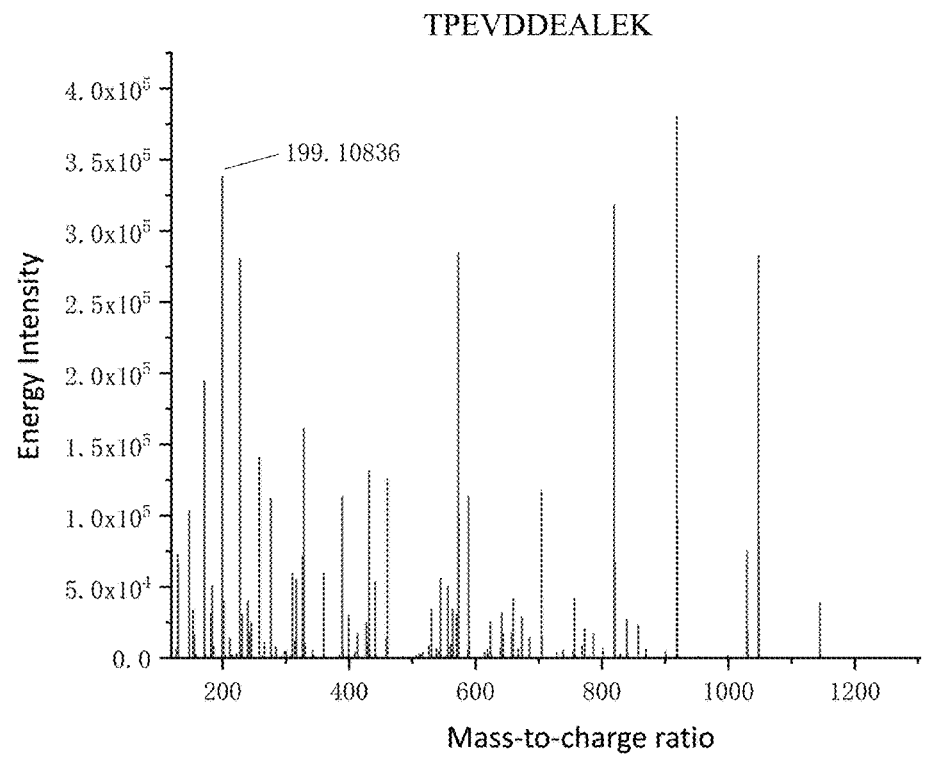
FIG. 5 is the full fragment ion diagram of the characteristic peptide segment (TPEVDDEALEK) shown in SEQ ID NO. 3.
Figure 6:
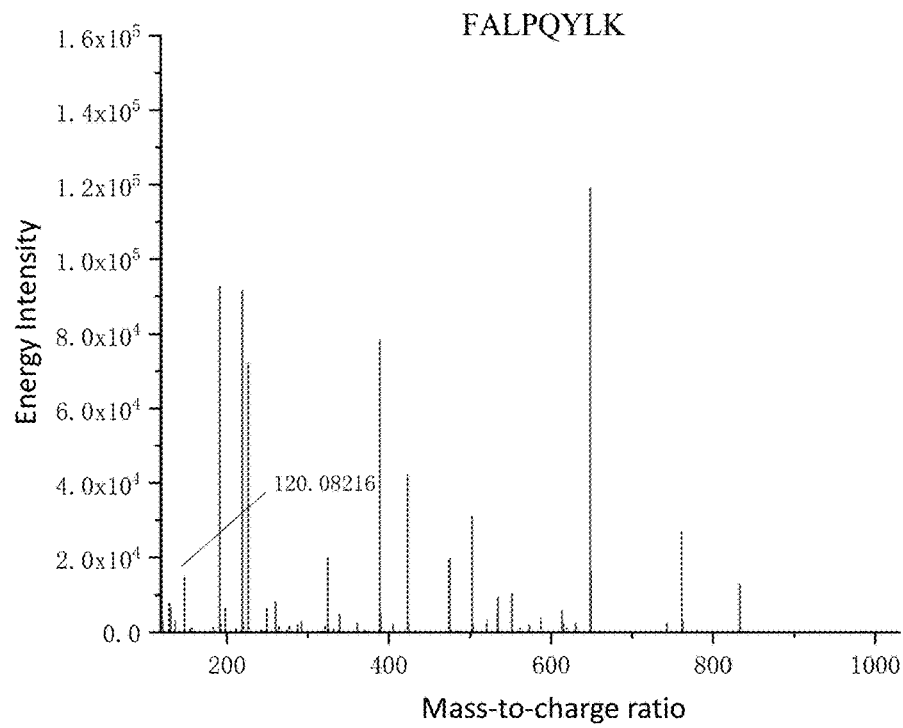
FIG. 6 is the full fragment ion diagram of the characteristic peptide segment (FALPQYLK) shown in SEQ ID NO. 4.
Figure 7:
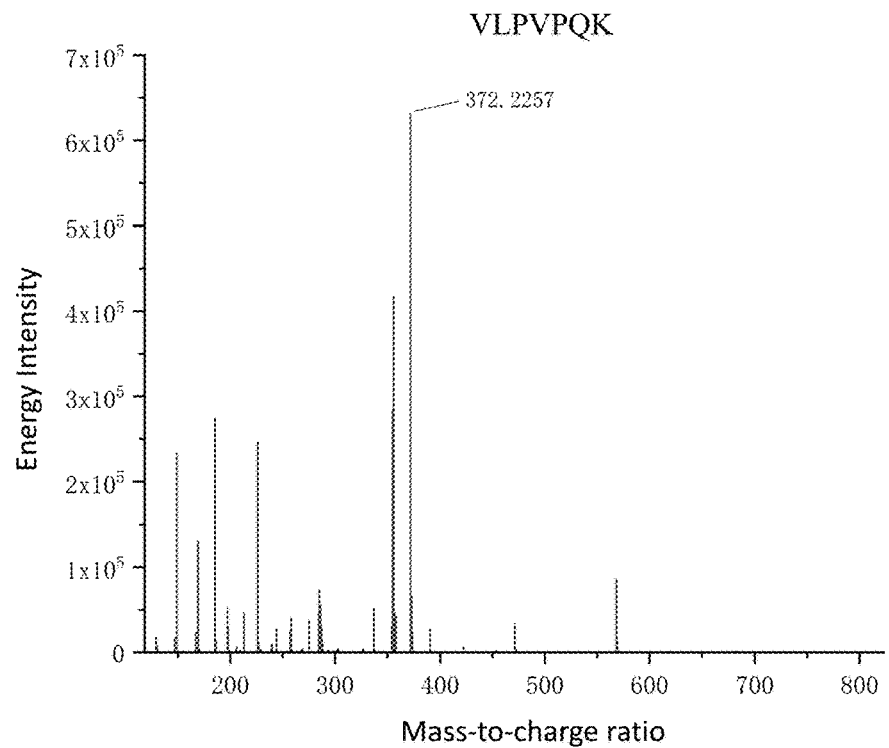
FIG. 7 is the full fragment ion diagram of the characteristic peptide segment (VLPVPQK) shown in SEQ ID NO. 2.

Specific information on the above four characteristic peptide segments was shown in Table 3, and their mass spectra in PRM mode were shown in FIG. 3.

Figure 8:
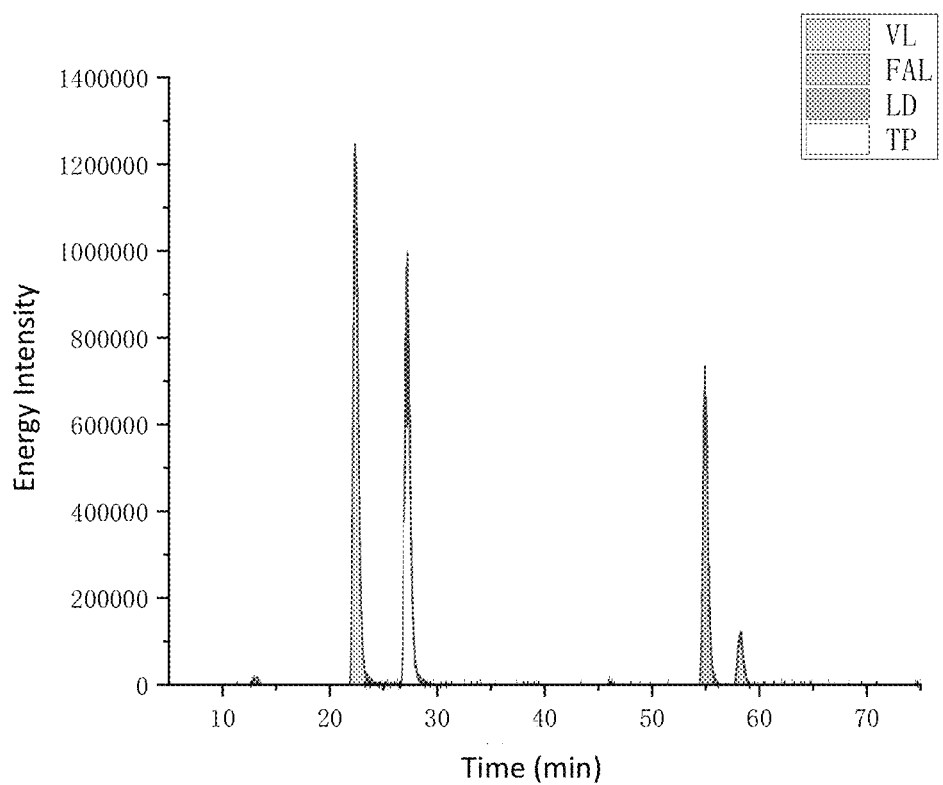
FIG. 8 is a quantitative daughter ion peak profile of four characteristic peptide segments.

The respective daughter ion information maps of the above four characteristic peptide segments were shown in FIGS. 4, 5, 6, and 7, respectively, from which it can be seen that the quantitative daughter ions selected in the experiment have higher response values in the detection process; FIG. 8 showed the daughter ion peaks of four peptide segments detected separately (here, they were combined into one diagram), to illustrate that they were independent peaks and did not interfere with each other during detection; in addition, the quantitative fragment ion information was shown in Table 4; and fragment ions with appropriate response value and mass number of each specific peptide segment were selected as quantitative ions.

Table 2.—Peptide segments produced by simulated digestion of α-lactalbumin, β-lactoglobulin, α-casein, and β-casein (SEQ ID NOS. 5-75 below)

β-Lactoglobulin
Protein sequence (SEQ ID NO. 5):

```
LIVTQTMKGL DIQKVAGTWY SLAMAASDIS LLDAQSAPLR

VYVEELKPTP EGDLEILLQKWENDECAQKK IIAEKTKIPA

VFKIDALNEN KVLVLDTDYK KYLLFCMENS

AEPEQSLVCQCLVRTPEVDD EALEKFDKAL KALPMHIRLS

FNPTQLEEQC HI
```

Peptide fragments by theoretical digestion (as shown below in SEQ ID NOS. 6-18, respectively):

| Mass | Position | # MC | Artificial Mod(s) | Mods | Peptide Sequence |
|---|---|---|---|---|---|
| 2707.3759 | 15-40 | 0 | | | VAGTWYSLA MAASDISLL DAQSAPLR (SEQ ID NO. 6) |
| 2675.2336 | 102-124 | 0 | Cys_CAM: 106, 119 121 | 2846.2980 | YLLFCMENS AEPEQSLVC QCLVR (SEQ ID NO. 7) |
| 2313.2587 | 41-60 | 0 | | | VYVEELKPT PEGDLEILL QK (SEQ ID NO. 8) |
| 1658.7843 | 149-162 | 0 | Cys_CAM: 160 | 1715.8057 | LSFNPTQLE EQCHI (SEQ ID NO. 9) |
| 1245.5845 | 125-135 | 0 | | | TPEVDDEAL EK (SEQ ID NO. 10) |
| 1122.4520 | 61 69 | 0 | Cys_CAM: 66 | 1179.4735 | WENDECAQK (SEQ ID NO. 11) |
| 1065.5826 | 92-100 | 0 | | | VLVLDTDYK (SEQ ID NO. 12) |
| 933.5437 | 1-8 | 0 | | | LIVTQTMK (SEQ ID NO. 13) |
| 916.4734 | 84-91 | 0 | | | IDALNENK (SEQ ID NO. 14) |
| 837.4763 | 142-148 | 0 | | | ALPMHIR (SEQ ID NO. 15) |
| 674.4235 | 78-83 | 0 | | | IPAVFK (SEQ ID NO. 16) |
| 673.3879 | 9-14 | 0 | | | GLDIQK (SEQ ID NO. 17) |
| 573.3606 | 71-75 | 0 | | | IIAEK (SEQ ID NO. 18) |

F Chain of Bovine α-Lactalbumin, Crystal Structure
Protein sequence (SEQ ID NO. 19):

```
EQLTKCEVFR ELKDLKGYGG VSLPEWVCTT FHTSGYDTQA

IVQNNDSTEY GLFQINNKIWCKDDQNPHSS NICNISCDKF

LDDDLTDDIM CVKKILDKVG INYWLAHKAL CSEKLDQWLCEKL
```

Peptide fragments by theoretical digestion (as shown below in SEQ ID NOS. 20-28, respectively):

| Mass | Position | # MC | Artificial Mod(s) | Mods | Peptide Sequence |
|---|---|---|---|---|---|
| 4654.1467 | 17-58 | 0 | Cys_CAM: 28 | 4711.1681 | GYGGVSLPE WVCTTFHTS GYDTQAIV QNNDSTEYG LFQINNK (SEQ ID NO. 20) |
| 1889.7752 | 63-79 | 0 | Cys_CAM: 73, 77 | 2003.8182 | DDQNPHSSN ICNISCDK (SEQ ID NO. 21) |

| Mass | Position | # MC | Artificial Mod(s) | Mods | Peptide Sequence |
|---|---|---|---|---|---|
| 1642.7338 | 80-93 | 0 | Cys_CAM: 91 | 1699.7553 | FLDDDLTDD IMCVK (SEQ ID NO. 22) |
| 1200.6524 | 99-108 | 0 | | | VGINYWLAH K (SEQ ID NO. 23) |
| 1034.4975 | 115-122 | 0 | Cys_CAM: 120 | 1091.5190 | LDQWLCEK (SEQ ID NO. 24) |
| 653.3075 | 6-10 | 0 | Cys_CAM: 6 | 710.3290 | CEVFR (SEQ ID NO. 25) |
| 650.3178 | 109-114 | 0 | Cys_CAM: 111 | 707.3392 | ALCSEK (SEQ ID NO. 26) |
| 618.3457 | 1-5 | 0 | | | EQLTK (SEQ ID NO. 27) |
| 549.2853 | 59-62 | 0 | Cys_CAM: 61 | 606.3068 | IWCK (SEQ ID NO. 28) |

α-S1-Casein, Partial [Bovine]
Protein sequence (SEQ ID NO. 29):

```
MKLLILTCLV AVALARPKHP IKHQGLPQEV LNENLLRFFV
APFPEVFGKE KVNELSKDIGSESTEDQAME DIKQMEAESI
SSSEEIVPNS VEQKHIQKED
VPSERYLGYLEQLLRLKKYKVPQLEIVPNS AEERLHSMKE
GIHAQQKEPM IGVNQELAYF YPE
```

Peptide fragments by theoretical digestion (as shown below in SEQ ID NOS. 30-42, respectively):

| Mass | Position | # MC | Artificial Mod(s) | Mods | Peptide Sequence |
|---|---|---|---|---|---|
| 2321.0813 | 74-94 | 0 | | | QMEAESISS SEEIVPNSV EQK (SEQ ID NO. 30) |
| 1899.8833 | 148-163 | 0 | | | EPMIGVNQE LAYFYPE (SEQ ID NO. 31) |
| 1767.7589 | 58-73 | 0 | | | DIGSESTED QAMEDIK (SEQ ID NO. 32) |
| 1759.9449 | 23-37 | 0 | | | HQGLPQEVL NENLLR (SEQ ID NO. 33) |
| 1694.0760 | 3-18 | 0 | Cys_CAM: 8 | 1751.0975 | LLILTCLVA VALARPK (SEQ ID NO. 34) |
| 1580.8278 | 121-134 | 0 | | | VPQLEIVPN SAEER (SEQ ID NO. 35) |
| 1334.7299 | 38-49 | 0 | | | FFVAPFPEV FGK (SEQ ID NO. 36) |
| 1267.7045 | 106-115 | 0 | | | YLGYLEQLLR (SEQ ID NO. 37) |
| 910.4741 | 140-147 | 0 | | | EGIHAQQK (SEQ ID NO. 38) |
| 831.3843 | 99-105 | 0 | | | EDVPSER (SEQ ID NO. 39) |
| 689.3828 | 52-57 | 0 | | | VNELSK (SEQ ID NO. 40) |
| 615.3283 | 135-139 | 0 | | | LHSMK (SEQ ID NO. 41) |
| 525.3143 | 95-98 | 0 | | | HIQK (SEQ ID NO. 42) |

α-S2-Casein Precursor [Bovine]
Protein sequence (SEQ ID NO. 43):

```
MKFFIFTCLL AVALAKNTME HVSSSEESII SQETYKQEKN
MAINPSKENL CSTFCKEVVRNANEEEYSIG SSSEESAEVA
TEEVKITVDD KHYQKALNEI NQFYQKFPQY
LQYLYQGPIVLNPWDQVKRN AVPITPTLNR EQLSTSEENS
KKTVDMESTE VFTKLTKLTE EEKNRLNFLKKISQRYQKFA
LPQYLKTVYQ HQKAMKPWIQ PKTKVIPYVR YL
```

Peptide fragments by theoretical digestion (as shown below as SEQ ID NOS. 44-63, respectively):

| Mass | Position | # MC | Artificial Mod(s) | Mods | Peptide Sequence |
|---|---|---|---|---|---|
| 2709.4075 | 107-128 | 0 | | | FPQYLQYLY QGPIVLNPW DQVK (SEQ ID NO. 44) |

-continued

| Mass | Position | # MC | Artificial Mod(s) | Mods | Peptide Sequence |
|---|---|---|---|---|---|
| 2688.1642 | 61-85 | 0 | | | NANEEEYSIGSSSEESAEVATEEVK (SEQ ID NO. 45) |
| 2299.0394 | 17-36 | 0 | | | NTMEHVSSSEESIISQETYK (SEQ ID NO. 46) |
| 1556.8909 | 3-16 | 0 | Cys_CAM: 8 | 1613.9123 | FFIFTCLLAVALAK (SEQ ID NO. 47) |
| 1386.6457 | 153-164 | 0 | | | TVDMESTEVFTK (SEQ ID NO. 48) |
| 1367.6954 | 96-106 | 0 | | | ALNEINQFYQK (SEQ ID NO. 49) |
| 1251.5699 | 141-151 | 0 | | | EQLSTSEENSK (SEQ ID NO. 50) |
| 1195.6793 | 130-140 | 0 | | | NAVPITPTLNR (SEQ ID NO. 51) |
| 1098.6128 | 204-212 | 0 | | | AMKPWIQPK (SEQ ID NO. 52) |
| 1044.4489 | 48-56 | 0 | Cys_CAM: 51, 55 | 1158.4918 | ENLCSTFCK (SEQ ID NO. 53) |
| 979.5611 | 189-196 | 0 | | | FALPQYLK (SEQ ID NO. 54) |
| 903.4683 | 197-203 | 0 | | | TVYQHQK (SEQ ID NO. 55) |
| 874.4451 | 40-47 | 0 | | | NMAINPSK (SEQ ID NO. 56) |
| 748.3723 | 168-173 | 0 | | | LTEEEK (SEQ ID NO. 57) |
| 746.4559 | 215-220 | 0 | | | VIPYVR (SEQ ID NO. 58) |
| 690.3668 | 86-91 | 0 | | | ITVDDK (SEQ ID NO. 59) |
| 634.3922 | 176-180 | 0 | | | LNFLK (SEQ ID NO. 60) |
| 575.2936 | 92-95 | 0 | | | HYQK (SEQ ID NO. 61) |
| 503.2936 | 182-185 | 0 | | | ISQR (SEQ ID NO. 62) |
| 502.2983 | 57-60 | 0 | | | EVVR (SEQ ID NO. 63) |

β-Casein

Protein sequence (SEQ ID NO. 64):

```
MKVLILACLV ALALARELEE LNVPGEIVES LSSSEESITR
INKKIEKFQS EEQQQTEDELQDKIHPFAQT QSLVYPFPGP
IHNSLPQNIP PLTQTPVVVP PFLQPEVMGV
SKVKEAMAPKHKEMPFPKYP VEPFTESQSL TLTDVENLHL
PLPLLQSWNH QPHQPLPPTV MFPPQSVLSLSQSKVLPYPQ
KAVPYPQRDM PIQAFLLYQE PVLGPVRGPF PIIV
```

Peptide fragments by theoretical digestion (as shown below in SEQ ID NOS. 65-75, respectively):

| Mass | Position | # MC | Artificial Mod(s) | Mods | Peptide Sequence |
|---|---|---|---|---|---|
| 6359.2558 | 129-184 | 0 | | | YPVEPFTESOSLTLTDVENLHLPLPLLQSWMHQPHQPLPPTVMFPPQSVLSLSQSK (SEQ ID NO. 65) |
| 5356.8594 | 64-112 | 0 | | | IHPFAQTQSLVYPFPGPIHNSLPQNIPPLTQTPVWPPFLQPEVMGVSK (SEQ ID NO. 66) |
| 2646.2992 | 17-40 | 0 | | | ELEELNVPGEIVESLSSSEESITR (SEQ ID NO. 67) |
| 2186.1678 | 199-217 | 0 | | | DMPIQAFLLYQEPVLGPVR (SEQ ID NO. 68) |
| 1981.8621 | 48-63 | 0 | | | FQSEEQQQTEDELQDK (SEQ ID NO. 69) |

-continued

| Mass | Position | # MC | Artificial Mod(s) | Mods | Peptide Sequence |
|---|---|---|---|---|---|
| 1438.9177 | 3-16 | 0 | | | VLILACLVA LALAR (SEQ ID NO. 70) |
| 830.4519 | 192-198 | 0 | Cys_CAM 8 1751.0975 | | AVPYPQR (SEQ ID NO. 71) |
| 780.4978 | 185-191 | 0 | | | VIPVPQK (SEQ ID NO. 72) |
| 748.3698 | 123-128 | 0 | | | EMPFPK (SEQ ID NO. 73) |
| 742.4497 | 218-224 | 0 | | | GPFPIIV (SEQ ID NO. 74) |
| 646.3228 | 115-120 | 0 | | | EAMAPK (SEQ ID NO. 75) |

TABLE 3

Information on characteristic peptide segments

| Protein | Peptide segment | Molecular weight | Amino acid chain |
|---|---|---|---|
| β-lg | TPEVDDEALEK (SEQ ID NO. 3) | 623.29 | Thr-Pro-Glu-Val-Asp-Asp-Glu-Ala-Leu-Glu-Lys |
| α-la | LDQWLCEK (SEQ ID NO. 1) | 546.23 | Leu-Asp-Gln-Trp-Leu-Cys-Glu-Lys |
| α-cs | FALPQYLK (SEQ ID NO. 4) | 490.19 | Phe-Ala-Leu-Pro-Gln-Tyr-Leu-Lys |
| β-cs | VLPVPQK (SEQ ID NO. 2) | 390.75 | Val-Leu-Pro-Val-Pro-Gln-Lys |

TABLE 4

Information on quantitative fragment ions

| Parent particle | Daughter ion mass number (KDa) | Retention time (min) |
|---|---|---|
| TPEVDDEALEK (SEQ ID NO. 3) | 199.10836 | 27.5 |
| LDQWLCEK (SEQ ID NO. 1) | 268.16794 | 55.2 |
| FALPQYLK (SEQ ID NO. 4) | 120.08216 | 57.8 |
| VLPVPQK (SEQ ID NO. 2) | 372.2257 | 23.7 |

Figure 9:
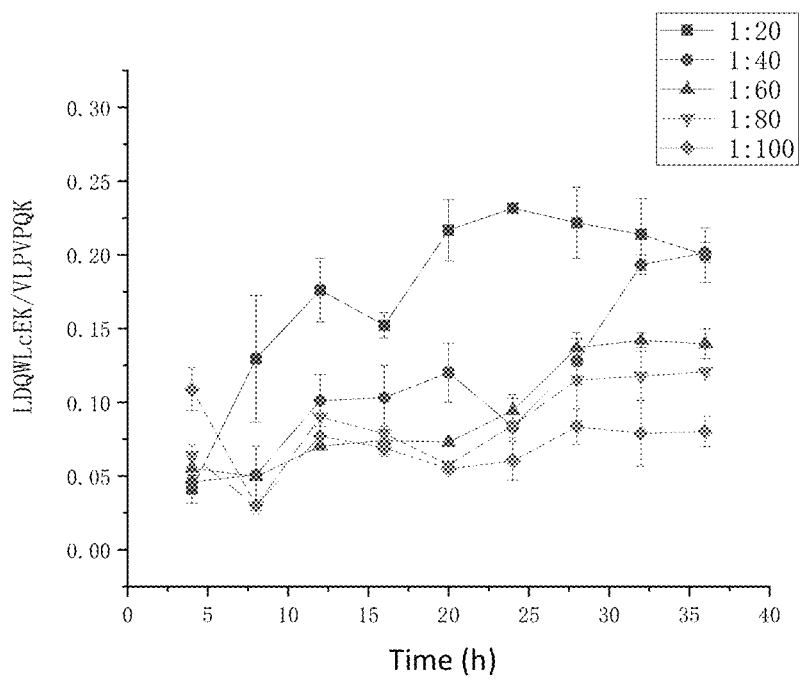
FIG. 9 shows the change of peak area ratio of characteristic peptide segments LDQWLCEK (SEQ ID NO. 1)/VLPVPQK (SEQ ID NO. 2) at different enzyme concentrations and with different enzymolysis time, with the enzymolysis time as abscissa, and the peak area ratio of two characteristic peptide segments as ordinate.
Figure 10:
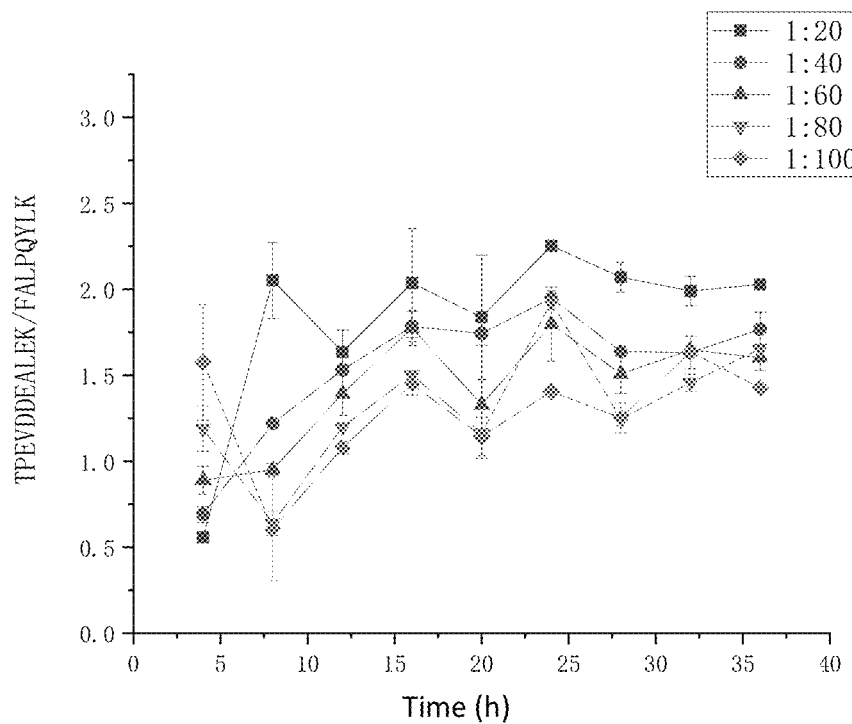
FIG. 10 shows the change of peak area ratio of characteristic peptide segments TPEVDDEALEK (SEQ ID NO. 3)/FALPQYLK (SEQ ID NO. 4) at different enzyme concentrations and with different enzymolysis time, with the enzymolysis time as abscissa, and the peak area ratio of two characteristic peptide segments as ordinate.

Example 2: Optimization of Enzymolysis Conditions, Selection of Substrate Concentration, as Well as Selection of Filter Membrane Optimization of Enzymolysis Conditions:

In this experiment, milk powder samples under the brand names Sanyuan and Ailiyou (with a protein concentration of 11.6 g/100 g milk powder sample) were used as substrates and subjected to enzymolysis at enzyme concentrations of 1:20, 1:40, 1:60, 1:80, and 1:100, respectively, according to the information provided by the product suppliers. As a result, an enzyme concentration of 1:20 and enzymolysis time of 28 h were selected based on variations in the peak area ratio of the characteristic peptide segments LDQWLCEK (SEQ ID NO. 1)/VLPVPQK (SEQ ID NO. 2) and variations in the peak area ratio of the characteristic peptide segments TPEVDDEALEK (SEQ ID NO. 3)/FALPQYLK (SEQ ID NO. 4) in the process of enzymolysis, both of which tended to be stable after enzymolysis for 28 h at the enzyme concentration of 1:20 (See FIGS. 9 and 10 for details).

Figure 11:
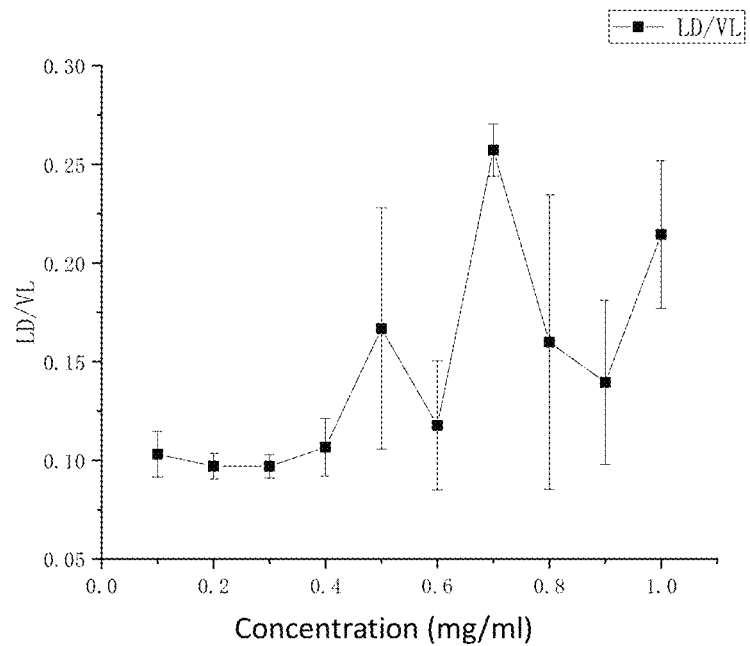
FIG. 11 shows the impact of different substrate concentrations on the peak area ratio of characteristic peptide segments LDQWLCEK (SEQ ID NO. 1)/VLPVPQK (SEQ ID NO. 2) at an enzyme concentration of 1:20 with enzymolysis time of 28 h, with the substrate concentration as abscissa, and the peak area ratio of two characteristic peptide segments as ordinate.
Figure 12:
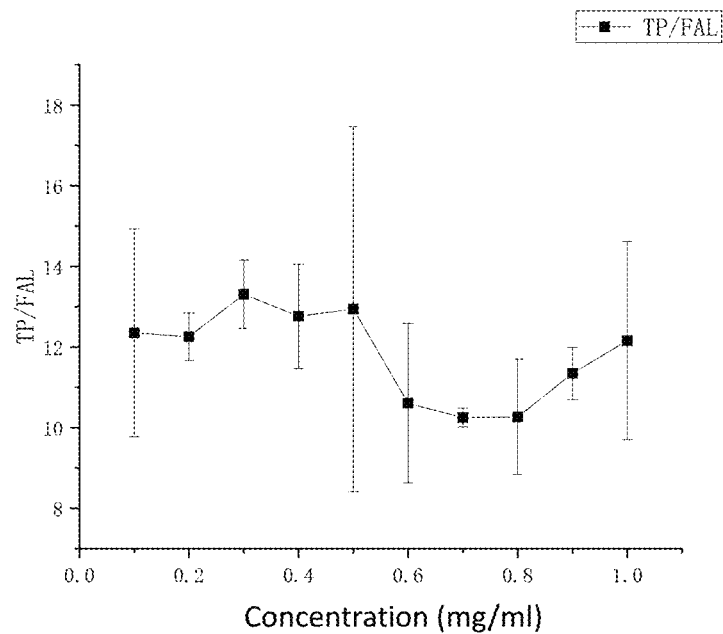
FIG. 12 shows the impact of different substrate concentrations on the peak area ratio of characteristic peptide segments TPEVDDEALEK (SEQ ID NO. 3)/FALPQYLK (SEQ ID NO. 4) at an enzyme concentration of 1:20 with enzymolysis time of 28 h, with the substrate concentration as abscissa, and the peak area ratio of two characteristic peptide segments as ordinate.

Selection of Substrate Concentration:

Milk powder samples were dissolved into solutions with ten protein concentration gradients between 0.1-1.0 mg/mL, which were then filtered roughly with pure acetic acid filter membrane with a pore size of 0.45 μm. 250 μL of sample solution was added to 150 μL of ammonium bicarbonate solution, followed by adding 10 μL of dithiothreitol solution, and kept in a water bath at 70° C. for 30 min. After cooling, 30 μL of iodoacetamide solution was added thereto, followed by standing for 30 min in the dark. After illuminating for 10 min, 10 μL of calcium chloride solution was added, followed by adding 50 μL of Trypsin solution, and then enzyme digestion was performed at 37° C. for 28 h, followed by adding 10 μL of acetic acid solution, and standing for 15 min to stop digestion. After filtration with 0.22 μm of polyethersulfone filter membrane, selective ion scanning analysis was carried out by nanoliter liquid chromatography. The results showed that when the protein concentration was below 0.4 mg/mL, the ratio of two characteristic peptide segments remained relatively stable after enzymolysis, indicating a good detection effect (See FIGS. 11 and 12).

Selection of Filter Membrane:

The pure acetic acid filter membrane having a large pore size of 0.45 nm was used to filter the milk powder sample preliminarily, to remove some additives, so as to avoid the impact thereof on the subsequent experiments and ensure the stability of the method. 0.22 μm of polyethersulfone filter membrane with extremely low protein adsorption was selected for filtration before running on machine.

Example 3: Detection Procedure of the Method of the Present Disclosure

1) Establishment of Standard Curve:

Four protein standard substances of α-lactalbumin, β-lactoglobulin, α-casein, and β-casein were used. Specifically, whey protein standard solution was prepared in accordance with α-lactalbumin and β-lactoglobulin accounting for 20% and 50% of whey protein, respectively (i.e., the contents of α-lactalbumin and β-lactoglobulin were 20% and 50%, respectively); and casein standard solution was prepared in accordance with α-casein and β-casein accounting for 50% and 40% of casein, respectively (i.e., the contents of α-casein and β-casein were 50% and 40%, respectively); and the prepared whey protein standard solution had the same concentration as the prepared casein standard solution.

Figure 13:
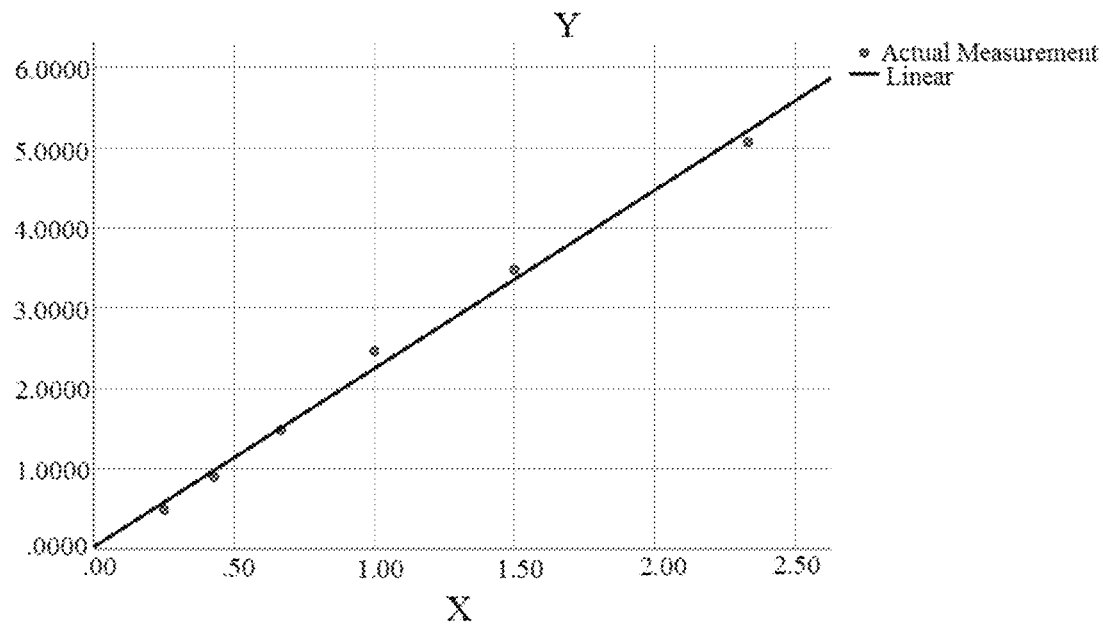
FIG. 13 is a standard curve of peak area ratio vs concentration ratio of characteristic peptide segments TPEVDDEALEK (SEQ ID NO. 3)/FALPQYLK (SEQ ID NO. 4), with the concentration ratio of two characteristic peptide segments as abscissa, and the peak area ratio thereof as ordinate; and R2 of the standard curve regression equation is 0.9935.
Figure 14:
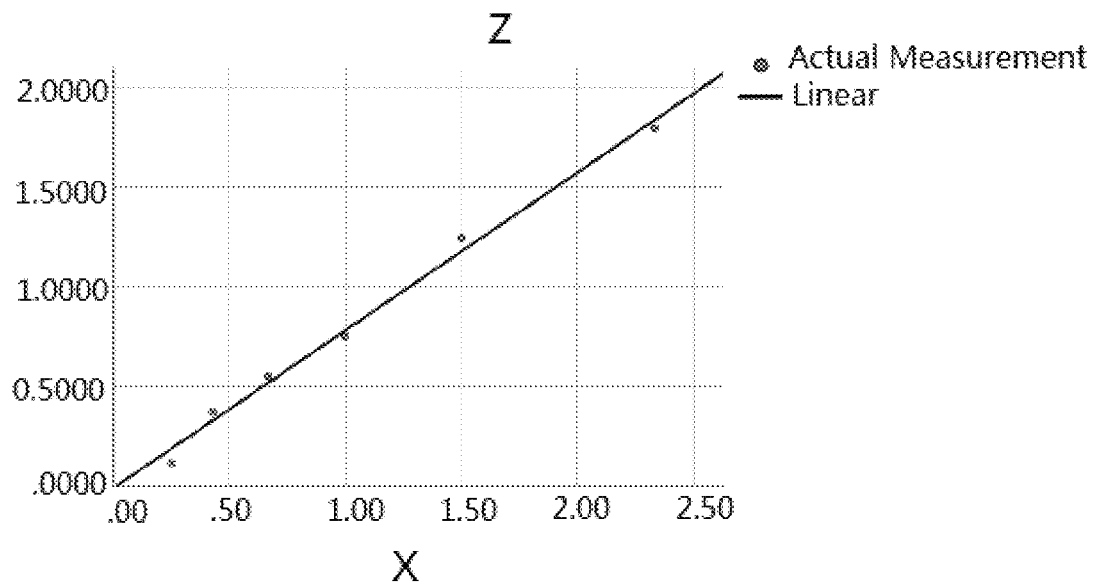
FIG. 14 is a standard curve of peak area ratio vs concentration ratio of characteristic peptide segments LDQWLCEK (SEQ ID NO. 1)/VLPVPQK (SEQ ID NO. 2), with the concentration ratio of two characteristic peptide segments as abscissa, and the peak area ratio thereof as ordinate; and R2 of the standard curve regression equation is 0.992.

Certain amounts of the whey protein standard solution and the casein standard solution prepared as above were mixed to prepare 1 mL of a mixed solution with a whey protein/casein ratio of 0.25, 0.43, 0.67, 1, 1.5, 2.33 (mass ratio), which was then detected for drawing standard curves; the standard curve of peak area ratio vs concentration ratio of characteristic peptide segments TPEVDDEALEK (SEQ ID NO. 3)/FALPQYLK (SEQ ID NO. 4) was shown in FIG. 13, and the standard curve of peak area ratio vs concentration ratio of characteristic peptide segments LDQWLCEK (SEQ ID NO. 1)/VLPVPQK (SEQ ID NO. 2) was shown in FIG. 14.

2) Treatment and Enzyme Digestion of Milk Powder Samples to be Tested:

Dissolving the milk powder sample to be tested into a sample solution with a protein concentration of 0.2 mg/ml; subjecting the sample solution to rough filtration with a pure acetic acid filter membrane with a pore size of 0.45 µm; adding the roughly filtered sample solution into ammonium bicarbonate solution, followed by adding dithiothreitol solution, and placing the mixture in a water bath at 70° C. for 30 min; after cooling, adding iodoacetamide solution thereto, and standing for 30 min in the dark; then illuminating for 10 min, followed by adding calcium chloride solution thereto; adding trypsin solution to allow an enzyme digestion at 37° C. for 26-30 h; adding acetic acid solution to stop the enzyme digestion;

3) filtering the enzymolysis products from step 2) with polyethersulfone filter membrane, and then performing selective ion scanning analysis by mass spectrometry to detect the peak area ratios of characteristic peptide segments of β-lactoglobulin to α-casein and of α-lactalbumin to β-casein in the milk powder;

4) substituting the peak area ratio of the characteristic peptide segments of β-lactoglobulin to α-casein in the milk powder as detected from step 3) into the standard curve to determine the ratio M of whey protein to casein, and calculating the actual amounts of β-lactoglobulin and α-casein based on the ratio M thus determined;

and, substituting the peak area ratio of the characteristic peptide segments of α-lactalbumin to β-casein in the milk powder as detected from step 3) into the standard curve to determine the ratio N of whey protein to casein, and calculating the actual amounts of α-lactalbumin to β-casein based on the ratio N thus determined;

the actual amounts of β-lactoglobulin and α-casein are calculated by the following formulas, respectively:

$$\beta\text{-lactoglobulin} = \frac{M1}{M1+M2}X*50\%, \alpha\text{-casein} = \frac{M2}{M1+M2}X*50\%;$$

wherein, M1 was the preceding term in the ratio M of whey protein:casein as determined based on the peak area ratio of characteristic peptide segments of β-lactoglobulin to α-casein, and M2 was the latter term in the ratio M of whey protein:casein as determined based on the peak area ratio of characteristic peptide segments of β-lactoglobulin to α-casein, with the provisions of: M=M1/M2, and M1+M2=1; and X is the total protein concentration of the sample;

the actual amounts of α-lactalbumin and β-casein are calculated by the following formulas, respectively:

$$\alpha\text{-}la = \frac{N1}{N1+N2}X*20\%, \beta\text{-}cs = \frac{N2}{N1+N2}X*40\%;$$

wherein, N1 was the preceding term in the ratio N of whey protein:casein as determined based on the peak area ratio of characteristic peptide segments of α-lactalbumin to β-casein, and N2 was the latter term in the ratio N of whey protein:casein as determined based on the peak area ratio of characteristic peptide segments of α-lactalbumin to β-casein, with the provisions of: N=N1/N2, and N1+N2=1; and X is the total protein concentration of the sample;

5) acquiring the actual contents of whey protein and casein, and/or the actual ratio of whey protein/casein based on the actual amounts of α-lactalbumin, β-casein, β-lactoglobulin, and α-casein obtained from step 4);

the formula for calculating the actual content of whey protein was:

$$\frac{\frac{N1}{N1+N2}X*20\% + \frac{M1}{M1+M2}X*50\%}{0.7}$$

the formula for calculating the actual content of casein was:

$$\frac{\frac{M2}{M1+M2}X*50\% + \frac{N2}{N1+N2}X*40\%}{0.9}$$

the formula for calculating the actual ratio of whey protein/casein was:

$$\frac{\frac{N1}{N1+N2}X*20\% + \frac{M1}{M1+M2}X*50\%}{0.7} \Big/$$

$$\frac{\frac{M2}{M1+M2}X*50\% + \frac{N2}{N1+N2}X*40\%}{0.9} =$$

$$\frac{18N1+45M1}{35M2+28N2} = \frac{63MN+18N+45M}{35N+28M+63};$$

wherein, M1 was the preceding term in the ratio M of whey protein:casein as determined based on the peak area ratio of characteristic peptide segments of β-lactoglobulin to α-casein, and M2 was the latter term in the ratio M of whey protein:casein as determined based on the peak area ratio of characteristic peptide segments of β-lactoglobulin to α-casein, with the provisions of: M=M1/M2, and M1+M2=1;

wherein, N1 was the preceding term in the ratio N of whey protein:casein as determined based on the peak area ratio of characteristic peptide segments of α-lactalbumin to β-casein, and N2 was the latter term in the ratio N of whey protein:casein as determined based on the peak area ratio of characteristic peptide segments of α-lactalbumin to β-casein, with the provisions of: N=N1/N2, and N1+N2=1; and, wherein, X is the total protein concentration of the sample.

Figure 15:
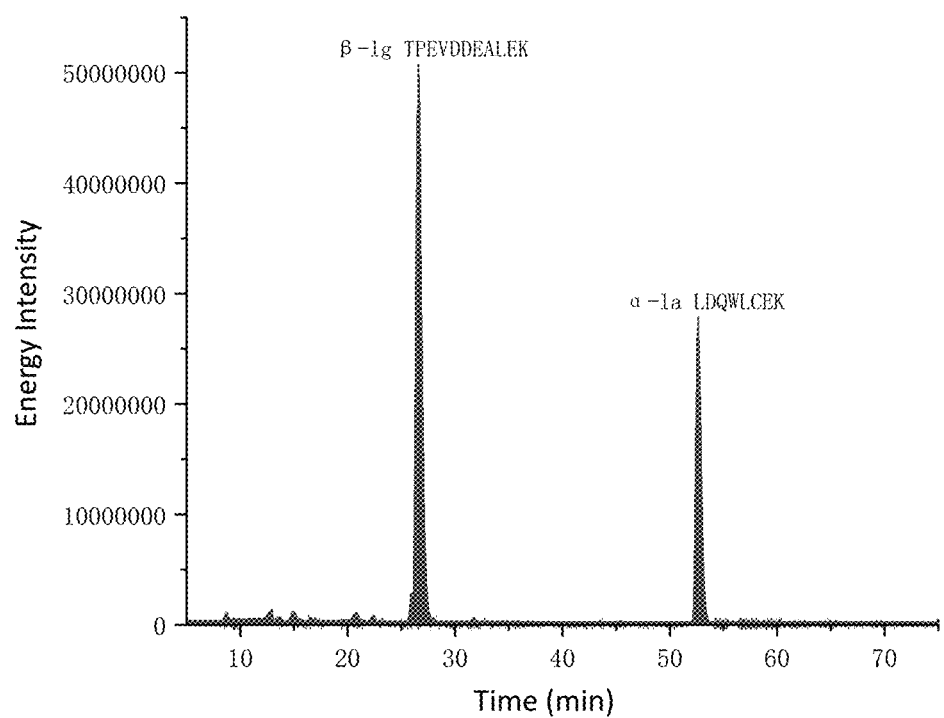
FIG. 15 is a primary mass spectrum of desalted whey powder.
Figure 16:
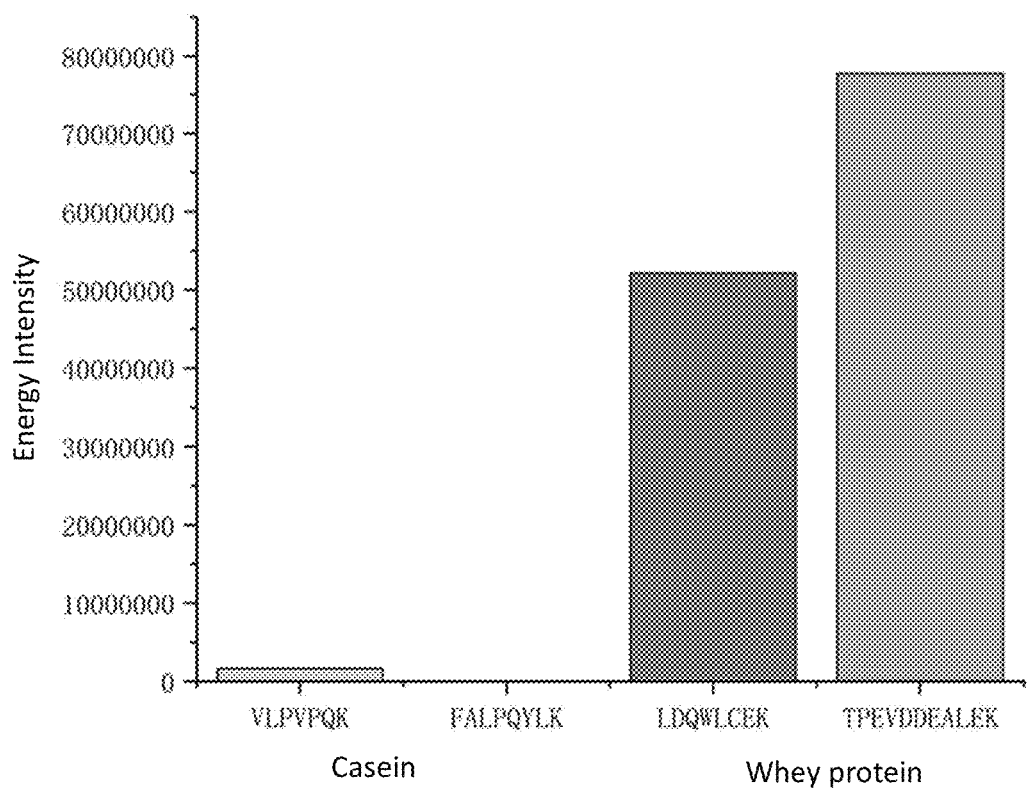
FIG. 16 shows the composition of desalted whey powder protein.

Example 4: Methodology Validation on the Detection Method of the Present Disclosure by Using Desalted Whey Powder Standard Addition Recovery Rate Desalted whey powder was used as the standard sample and was known to have a protein content of 12% according to its product annotation, which was almost made up of whey protein, with only a very little or negligible amount of casein, as detected by an instrument; the primary mass spectrum of the desalted whey powder was shown in FIG. 15 and analyzed to obtain its composition as shown in FIG. 16.

the detection method of the present disclosure was verified by using the desalted whey powder and the results were shown in Table 5 below.

TABLE 5

|  | Added amount (mg) | Theoretical value (mg) | Detection value (mg) | Recovery rate (%) | RSD (%) |
|---|---|---|---|---|---|
| Substrate | 0 | / | 19.48 | / | 7.35 |
| Desalted whey powder | 3.60 | 23.08 | 23.03 | 98.63 | 0.84 |
|  | 7.20 | 26.68 | 26.90 | 103.06 | 7.42 |
|  | 10.80 | 30.28 | 31.72 | 113.33 | 1.83 |
|  | 14.40 | 33.88 | 34.11 | 101.62 | 0.84 |

According to Table 5, the standard addition recovery rate of the desalted whey powder detected by the detection method of the present disclosure was 98.63%-113.33%, and the corresponding RSD was 0.84%-7.42%.

Example 5: Methodology Validation on the Detection Method of the Present Disclosure by Using Commercial Formula Milk Powder According to the detection method of the present disclosure described in Example 3, three brands of commercial formula milk powder were tested, in which: 6 groups of parallel tests were conducted once a day for 3 days to verify the repeatability and precision of the detection method of the present disclosure; the detection results of the three brands of commercial formula milk powder were shown in Tables 6-8, in which, LD represents the characteristic peptide segment of α-lactalbumin, LDQWLCEK (SEQ ID NO. 1), TP represents the characteristic peptide segment of β-lactoglobulin, TPEVDDEALEK (SEQ ID NO. 3), FAL represents the characteristic peptide segment of α-casein, FALPQYLK (SEQ ID NO. 4), and VL represents the characteristic peptide segment of β-casein, VLPVPQK (SEQ ID NO. 2).

TABLE 6

Repeatability and precision results of the detection of 1# brand formula milk powder (Sanyuan, Enbeiyi, Section 1)

|  | Days | | | | | |
|---|---|---|---|---|---|---|
|  | 1 | | 2 | | 3 | |
|  | TP/FAL | LD/VL | TP/FAL | LD/VL | TP/FAL | LD/VL |
|  | 5.661328 | 0.596471 | 5.943357 | 0.593253 | 5.854161 | 0.594823 |
|  | 6.698231 | 0.591934 | 6.182401 | 0.636411 | 6.215530 | 0.601842 |
|  | 5.833083 | 0.626097 | 6.463053 | 0.658798 | 6.251452 | 0.620248 |
|  | 6.070490 | 0.592644 | 5.611366 | 0.614108 | 5.950025 | 0.581455 |
|  | 6.191200 | 0.604171 | 5.853564 | 0.582013 | 6.072519 | 0.562768 |
|  | 6.120052 | 0.558423 | 6.115780 | 0.597187 | 6.182007 | 0.561523 |
| Average | 6.095731 | 0.594957 | 6.028253 | 0.613628 | 6.087616 | 0.587110 |
| SD | 0.355257 | 0.021937 | 0.293936 | 0.029136 | 0.158603 | 0.023038 |
| RSD (%) | 0.058280 | 0.036871 | 0.04876 | 0.047482 | 0.026053 | 0.039241 |
| Average between groups | 6.070533 | | | 0.598565 | | |
| SD | 0.036840 | | | 0.013623 | | |
| RSD (%) | 0.006069 | | | 0.022759 | | |

TABLE 7

Repeatability and precision results of the detection of 2# brand formula milk powder (Sanyuan, Aixinbao, Section 1)

|  | Days | | | | | |
|---|---|---|---|---|---|---|
|  | 1 | | 2 | | 3 | |
|  | TP/FAL | LD/VL | TP/FAL | LD/VL | TP/FAL | LD/VL |
|  | 6.255670 | 0.611835 | 5.629679 | 0.615912 | 5.666182 | 0.586044 |
|  | 5.760567 | 0.605571 | 5.619842 | 0.648726 | 5.724010 | 0.538855 |
|  | 6.331991 | 0.590981 | 5.304704 | 0.630166 | 5.634282 | 0.574862 |
|  | 6.156652 | 0.634878 | 5.836408 | 0.631432 | 5.471585 | 0.574179 |
|  | 5.802848 | 0.562343 | 5.592876 | 0.613239 | 5.762156 | 0.532703 |
|  | 5.901041 | 0.552298 | 5.636404 | 0.627743 | 5.465830 | 0.576933 |

TABLE 7-continued

Repeatability and precision results of the detection of 2# brand formula milk powder (Sanyuan, Aixinbao, Section 1)

| | Days | | | | | |
|---|---|---|---|---|---|---|
| | 1 | | 2 | | 3 | |
| | TP/FAL | LD/VL | TP/FAL | LD/VL | TP/FAL | LD/VL |
| Average | 6.034795 | 0.592984 | 5.603319 | 0.627870 | 5.620674 | 0.563929 |
| SD | 0.244480 | 0.031200 | 0.170689 | 0.012728 | 0.125822 | 0.022300 |
| RSD (%) | 0.040512 | 0.052615 | 0.030462 | 0.020272 | 0.022386 | 0.039545 |
| Average between groups | 5.834348 | | | 0.605599 | | |
| SD | 0.244257 | | | 0.032015 | | |
| RSD (%) | 0.041865 | | | 0.052864 | | |

TABLE 8

Repeatability and precision results of the detection of 3# brand formula milk powder (Sanyuan, Ailiyou, Section 1)

| | Days | | | | | |
|---|---|---|---|---|---|---|
| | 1 | | 2 | | 3 | |
| | TP/FAL | LD/VL | TP/FAL | LD/VL | TP/FAL | LD/VL |
| | 7.453970 | 0.531694 | 7.704645 | 0.561678 | 6.723771 | 0.593539 |
| | 7.259978 | 0.595509 | 7.603946 | 0.570701 | 8.520871 | 0.662325 |
| | 7.114793 | 0.510083 | 7.885622 | 0.638107 | 8.433776 | 0.676738 |
| | 7.299271 | 0.476919 | 7.420642 | 0.548663 | 8.070415 | 0.759728 |
| | 7.429340 | 0.553053 | 7.749015 | 0.577207 | 8.319099 | 0.720309 |
| | 7.765910 | 0.583946 | 7.761472 | 0.602464 | 7.881502 | 0.613721 |
| Average | 7.387210 | 0.541867 | 7.687557 | 0.583137 | 7.991573 | 0.671060 |
| SD | 0.222611 | 0.044956 | 0.159372 | 0.032354 | 0.664624 | 0.062759 |
| RSD (%) | 0.030135 | 0.082965 | 0.020731 | 0.055483 | 0.083166 | 0.093522 |
| Average between groups | 7.688780 | | | 0.598688 | | |
| SD | 0.302183 | | | 0.065985 | | |
| RSD (%) | 0.039302 | | | 0.110217 | | |

According to Tables 6-8, the RSD within groups for the above detections was in the range of 2.03%-9.35%, and the RSD between groups was in the range of 0.61%-11.02%, indicating that the detection method of the present disclosure had good repeatability and precision.

Example 6: Detection Example of the Detection Method of the Present Disclosure

According to the detection method of the present disclosure described in Example 3, the content of whey protein in commercial formula milk powder (Abbott, Classic Enmeili, Section 1) was detected, and the specific procedure was as follows:

To 0.2 g commercial formula milk powder (Abbott, Classic Enmeili Section 1), ultrapure water was added to a fixed volume of 200 mL. The obtained sample solution was then filtered roughly with pure acetic acid filter membrane with a pore size of 0.45 μm. Then 250 μL of the filtered sample solution was added to 150 μL of ammonium bicarbonate solution, followed by adding 10 μL of dithiothreitol solution, and kept in a water bath at 70° C. for 30 min. After cooling to room temperature, 30 μL of iodoacetamide solution was added thereto, and allowed to stand for 30 min in the dark. After illuminating for 10 min, 10 μL of calcium chloride solution was added thereto, followed by adding 50 μL of Trypsin solution to allow an enzyme digestion at 37° C. for 28 h, and further followed by adding 10 μL of acetic acid solution and standing for 15 min to stop digestion. Filtration was carried out with 0.22 μm of polyethersulfone filter membrane prior to detection on the machine. It was calculated that whey protein accounted for 61.77% of the total protein content in the sample.

Finally, it should be noted that the above embodiments are only used to illustrate the technical solutions of the present disclosure, but not to limit it; although the present disclosure has been described in detail with reference to the foregoing embodiments, it will be understood by one of ordinary skill in the art that the technical solutions described in the foregoing embodiments can still be modified or some technical features can be equivalently substituted; however, these modifications or substitutions do not make the essence of the corresponding technical solutions departing from the spirit and scope of the technical solutions of various embodiments of the present disclosure.

The invention claimed is:

1. A method for detecting the contents of whey protein and casein, and/or the ratio thereof in milk powder by liquid chromatography-mass spectrometry, comprising:
   1) Preparing a standard solution of whey protein with the characteristic peptide segments of α-lactalbumin and β-lactoglobulin, in accordance with the α-lactalbumin and β-lactoglobulin accounting for 20% and 50% of the whey protein, respectively;
   2) Preparing a standard solution of casein with the characteristic peptide segments of α-casein and β-casein, in accordance with the α-casein and β-casein accounting for 50% and 40% of the casein, respectively;
   3) Mixing the standard solution of whey protein from step 1) with the standard solution of casein from step 2) to prepare a series of mixed protein standard solutions with a series of whey protein:casein ratios;
   4) Drawing standard curves with the ratio of whey protein to casein as abscissa and the peak area ratios of characteristic peptide segments of α-lactalbumin to β-casein and the peak area ratios of characteristic peptide segments of β-lactoglobulin to α-casein as ordinate;
   5) Detecting the milk powder to be tested for the peak area ratios of the characteristic peptide segments of β-lactoglobulin to α-casein and the peak area ratios of the characteristic peptide segments of α-lactalbumin to β-casein;
   6) Substituting the peak area ratio of the characteristic peptide segments of β-lactoglobulin to α-casein in the detected milk powder into the standard curve to determine the ratio M of whey protein to casein, and calculate the actual amounts of β-lactoglobulin and α-casein based on the ratio M thus determined;

and, substituting the peak area ratio of the characteristic peptide segments of α-lactalbumin to β-casein in the detected milk powder into the standard curve to determine the ratio N of whey protein to casein, and calculate the actual amounts of α-lactalbumin to β-casein based on the ratio N thus determined;

7) Acquiring the actual contents of whey protein and casein, and/or the actual ratio of whey protein/casein based on the actual amounts of α-lactalbumin, β-casein, β-lactoglobulin, and α-casein obtained from step 6).

2. The method according to claim 1, wherein the characteristic peptide segments of α-lactalbumin, β-casein, β-lactoglobulin, and α-casein are LDQWLCEK shown in SEQ ID NO. 1, VLPVPQK shown in SEQ ID NO. 2, TPEVDDEALEK shown in SEQ ID NO. 3, and FALPQYLK shown in SEQ ID NO. 4, respectively.

3. The method according to claim 1, wherein in step 3), the series of whey protein:casein ratios include whey protein:casein ratios of 0.25, 0.43, 0.67, 1, 1.5, and 2.33, respectively.

4. The method according to claim 1, wherein in step 6), the actual amounts of β-lactoglobulin and α-casein are calculated by the following formulas, respectively:

$$\beta\text{-lactoglobulin} = \frac{M1}{M1+M2} X * 50\%, \quad \alpha\text{-casein} = \frac{M2}{M1+M2} X * 50\%;$$

wherein M1 is the preceding term in the ratio M of whey protein:casein as determined based on the peak area ratio of characteristic peptide segments of β-lactoglobulin to α-casein, and M2 is the latter term in the ratio M of whey protein:casein as determined based on the peak area ratio of characteristic peptide segments of β-lactoglobulin to α-casein, with the provisions of: M=M1/M2, and M1+M2=1; and wherein X is the total protein concentration of the sample.

5. The method according to claim 1, wherein in step 6), the actual amounts of α-lactalbumin and β-casein are calculated by the following formulas, respectively:

$$\alpha\text{-}la = \frac{N1}{N1+N2} X * 20\%, \quad \beta\text{-}cs = \frac{N2}{N1+N2} X * 40\%;$$

wherein N1 is the preceding term in the ratio N of whey protein:casein as determined based on the peak area ratio of characteristic peptide segments of α-lactalbumin to β-casein, and N2 is the latter term in the ratio N of whey protein:casein as determined based on the peak area ratio of characteristic peptide segments of α-lactalbumin to β-casein, with the provisions of: N=N1/N2, and N1+N2=1; and, wherein, X is the total protein concentration of the sample.

6. The method according to claim 1, wherein, in step 7), the formula for calculating the actual content of whey protein is:

$$\frac{\frac{N1}{N1+N2} X * 20\% + \frac{M1}{M1+M2} X * 50\%}{0.7}$$

the formula for calculating the actual content of casein is:

$$\frac{\frac{M2}{M1+M2} X * 50\% + \frac{N2}{N1+N2} X * 40\%}{0.9}$$

the formula for calculating the actual ratio of whey protein/casein is:

$$\frac{\frac{N1}{N1+N2} X * 20\% + \frac{M1}{M1+M2} X * 50\%}{0.7} \Big/$$

$$\frac{\frac{M2}{M1+M2} X * 50\% + \frac{N2}{N1+N2} X * 40\%}{0.9} =$$

$$\frac{18N1 + 45M1}{35M2 + 28N2} = \frac{63MN + 18N + 45M}{35N + 28M + 63};$$

wherein M1 is the preceding term in the ratio M of whey protein:casein as determined based on the peak area ratio of characteristic peptide segments of β-lactoglobulin to α-casein, and M2 is the latter term in the ratio M of whey protein:casein as determined based on the peak area ratio of characteristic peptide segments of β-lactoglobulin to α-casein, with the provisions of: M=M1/M2, and M1+M2=1;

wherein N1 is the preceding term in the ratio N of whey protein:casein as determined based on the peak area ratio of characteristic peptide segments of α-lactalbumin to β-casein, and N2 is the latter term in the ratio N of whey protein:casein as determined based on the peak area ratio of characteristic peptide segments of α-lactalbumin to β-casein, with the provisions of: N=N1/N2, and N1+N2=1; and wherein X is the total protein concentration of the sample.

7. The method according to claim 1, wherein, the detection in step 5) comprises the steps of sample treatment and enzyme digestion:

dissolving the milk powder sample to be tested into a sample solution with a protein concentration of 0.1-0.4 mg/ml;

subjecting the sample solution to rough filtration with a pure acetic acid filter membrane with a pore size of 0.45 μm;

adding the roughly filtered sample solution into ammonium bicarbonate solution, followed by adding dithiothreitol solution, and standing in a water bath at 65-75° C. for 25-35 min; after cooling, adding iodoacetamide solution, and standing for 25-35 min in the dark;

illuminating the mixture for 8-12 min, followed by adding calcium chloride solution; then adding trypsin solution to allow an enzyme digestion at 37° C. for 26-30 h; then adding acetic acid solution to stop the enzyme digestion;

filtering the reaction mixture with polyethersulfone filter membrane, and then performing selective ion scanning analysis by mass spectrometry.

8. The method according to claim 1, wherein the upper detection limit of the method is at a total protein concentration of 0.4 mg/mL.

9. A combination of characteristic peptide segments for detecting the ratio of whey protein:casein by liquid chromatography-mass spectrometry, comprising: characteristic peptide segments of α-lactalbumin, β-casein, β-lactoglobulin, and α-casein with amino acid sequences as shown in SEQ ID NO. 1, SEQ ID NO. 2, SEQ ID NO. 3, and SEQ ID NO. 4, respectively.

10. The combination of characteristic peptide segments according to claim 9, which consists of the characteristic peptide segments of α-lactalbumin, β-casein, β-lactoglobulin, and α-casein with amino acid sequences as shown in SEQ ID NO. 1, SEQ ID NO. 2, SEQ ID NO. 3, and SEQ ID NO. 4, respectively.

\* \* \* \* \*